United States Patent
Chang et al.

(10) Patent No.: US 10,280,399 B2
(45) Date of Patent: May 7, 2019

(54) METHOD FOR DIFFERENTIATION OF NEURAL STEM CELLS, NEURONS AND GABAERGIC NEURONS FROM MESENCHYMAL STEM CELLS

(71) Applicant: SNU R&DB Foundation, Seoul (KR)

(72) Inventors: Mi Sook Chang, Seoul (KR); Ji Hye Park, Seoul (KR)

(73) Assignee: SNU R&DB FOUNDATION, Seoul (KR)

(*) Notice: Subject to any disclaimer, the term of this patent is extended or adjusted under 35 U.S.C. 154(b) by 190 days.

(21) Appl. No.: 15/366,515

(22) Filed: Dec. 1, 2016

(65) Prior Publication Data

US 2017/0292112 A1    Oct. 12, 2017

(30) Foreign Application Priority Data

Apr. 12, 2016   (KR) .................. 10-2016-0044968

(51) Int. Cl.
*C12N 5/00* (2006.01)
*C12N 5/0793* (2010.01)
*C12N 5/0797* (2010.01)

(52) U.S. Cl.
CPC ......... *C12N 5/0619* (2013.01); *C12N 5/0018* (2013.01); *C12N 5/0623* (2013.01); *C12N 2500/38* (2013.01); *C12N 2500/40* (2013.01); *C12N 2501/11* (2013.01); *C12N 2501/115* (2013.01); *C12N 2501/13* (2013.01); *C12N 2501/40* (2013.01); *C12N 2501/999* (2013.01); *C12N 2506/1384* (2013.01)

(58) Field of Classification Search
None
See application file for complete search history.

(56) References Cited

U.S. PATENT DOCUMENTS

| | | | |
|---|---|---|---|
| 10,017,734 B2* | 7/2018 | Shoji .................... | C12N 5/0619 |
| 2009/0004661 A1* | 1/2009 | Shetty .................. | C12N 5/0619 435/6.14 |
| 2014/0186305 A1* | 7/2014 | Rezina ................. | C12N 5/0606 424/93.7 |
| 2015/0010514 A1* | 1/2015 | Studer .................. | C12N 5/0619 424/93.7 |
| 2016/0177260 A1* | 6/2016 | Shoji .................... | C12N 5/0619 424/93.21 |

* cited by examiner

*Primary Examiner* — Blaine Lankford
(74) *Attorney, Agent, or Firm* — The PL Law Group, PLLC

(57) ABSTRACT

A method for differentiation of neural stem cells, neurons and GABAergic neurons from mesenchymal stem cells includes culturing the mesenchymal stem cells in a medium containing SB431542, Noggin and LDN193189. By this method, the mesenchymal stem cells are differentiated into neural stem cells, neurons and GABAergic neurons at a high transformation rate without gene manipulation.

11 Claims, 28 Drawing Sheets
Specification includes a Sequence Listing.

FIG. 4B

|  | Markers | Percentage |
|---|---|---|
| Single⁺ Cells | TuJ1⁺ | 90.37 ± 4.81 |
|  | PAX6⁺ | 79.17 ± 3.45 |
|  | NeuN⁺ | 83.27 ± 1.40 |
|  | MAP2⁺ | 77.09 ± 7.09 |
|  | S100⁺ | 27.27 ± 6.41 |
|  | GFAP⁺ | 33.10 ± 13.74 |
|  | OLIG2⁺ | 17.53 ± 2.80 |
| Double⁺ Cells | PAX6⁺/TuJ1⁺ | 75.16 ± 4.78 |
|  | MAP2⁺/NeuN⁺ | 78.30 ± 2.12 |
|  | GFAP⁺/S100⁺ | 25.45 ± 3.69 |
|  | OLIG2⁺/MAP2⁺ | 5.50 ± 0.51 |

FIG. 5C

|  | Markers | Percentage |
|---|---|---|
| Single⁺ Cells | TuJ1⁺ | 93.04 ± 2.12 |
|  | NKX2.1⁺ | 84.29 ± 3.84 |
|  | DLX2⁺ | 86.02 ± 1.27 |
|  | MAP2⁺ | 91.54 ± 3.27 |
|  | LHX6⁺ | 70.84 ± 5.54 |
| Double⁺ Cells | NKX2.1⁺/TuJ1⁺ | 78.15 ± 5.35 |
|  | DLX2⁺/TuJ1⁺ | 84.43 ± 2.00 |
|  | LHX6⁺/MAP2⁺ | 69.35 ± 5.53 |

FIG. 6C

|  | Markers | Percentage |
|---|---|---|
| Single⁺ Cells | MAP2⁺ | 95.56 ± 1.32 |
|  | GABA⁺ | 46.64 ± 8.82 |
|  | GAD⁺ | 68.69 ± 9.70 |
| Double⁺ Cells | GABA⁺/MAP2⁺ | 46.64 ± 8.82 |
|  | GAD⁺/MAP2⁺ | 67.30 ± 10.59 |

SEQUENCE LISTING

```
<160> NUMBER OF SEQ ID NOS: 52

<210> SEQ ID NO 1
<211> LENGTH: 19
<212> TYPE: DNA
<213> ORGANISM: Artificial Sequence
<220> FEATURE:
<223> OTHER INFORMATION: primer

<400> SEQUENCE: 1
ctccaggaat acacccaaa                                                19

<210> SEQ ID NO 2
<211> LENGTH: 20
<212> TYPE: DNA
```

```
<213> ORGANISM: Artificial Sequence
<220> FEATURE:
<223> OTHER INFORMATION: primer

<400> SEQUENCE: 2
cagctcatgc tcgtcaatgt                                               20

<210> SEQ ID NO 3
<211> LENGTH: 20
<212> TYPE: DNA
<213> ORGANISM: Artificial Sequence
<220> FEATURE:
<223> OTHER INFORMATION: primer

<400> SEQUENCE: 3
gcacatgggt tcctaccagt                                               20

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
tccttctcag gctcgttgtt                                               20

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
ccaaccagcc agagaaagaa                                               20

<210> SEQ ID NO 6
<211> LENGTH: 20
<212> TYPE: DNA
<213> ORGANISM: Artificial Sequence
<220> FEATURE:
<223> OTHER INFORMATION: primer

<400> SEQUENCE: 6
gcaaggcgag gtactgagtc                                               20

<210> SEQ ID NO 7
<211> LENGTH: 21
<212> TYPE: DNA
<213> ORGANISM: Artificial Sequence
<220> FEATURE:
<223> OTHER INFORMATION: primer

<400> SEQUENCE: 7
aagcgcggct ttaccataga g                                             21

<210> SEQ ID NO 8
<211> LENGTH: 19
<212> TYPE: DNA
<213> ORGANISM: Artificial Sequence
<220> FEATURE:
<223> OTHER INFORMATION: primer

<400> SEQUENCE: 8
gctggggtga gggtagttg                                                19
```

<210> SEQ ID NO 9
<211> LENGTH: 21
<212> TYPE: DNA
<213> ORGANISM: Artificial Sequence
<220> FEATURE:
<223> OTHER INFORMATION: primer

<400> SEQUENCE: 9
agaagaacgg caagtacgag a                                            21

<210> SEQ ID NO 10
<211> LENGTH: 21
<212> TYPE: DNA
<213> ORGANISM: Artificial Sequence
<220> FEATURE:
<223> OTHER INFORMATION: primer

<400> SEQUENCE: 10
tgttgaggga cagattgtgg c                                            21

<210> SEQ ID NO 11
<211> LENGTH: 21
<212> TYPE: DNA
<213> ORGANISM: Artificial Sequence
<220> FEATURE:
<223> OTHER INFORMATION: primer

<400> SEQUENCE: 11
ggattgggag agcgtgtaac c                                            21

<210> SEQ ID NO 12
<211> LENGTH: 19
<212> TYPE: DNA
<213> ORGANISM: Artificial Sequence
<220> FEATURE:
<223> OTHER INFORMATION: primer

<400> SEQUENCE: 12
tgaaacgggt ccgaaactg                                               19

<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
gttcaagctg aatgcccaat                                              20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
acctagagcc atcaggagca                                              20

<210> SEQ ID NO 15
<211> LENGTH: 19
<212> TYPE: DNA
<213> ORGANISM: Artificial Sequence
<220> FEATURE:

```
<223> OTHER INFORMATION: primer

<400> SEQUENCE: 15
atcttggatg ggctcttgg                                                    19

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
tgtactccat ttccgtgtcg                                                   20

<210> SEQ ID NO 17
<211> LENGTH: 20
<212> TYPE: DNA
<213> ORGANISM: Artificial Sequence
<220> FEATURE:
<223> OTHER INFORMATION: primer

<400> SEQUENCE: 17
ggtggctcca gtgattaaag                                                   20

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
tgtccaaggc gttctatttc                                                   20

<210> SEQ ID NO 19
<211> LENGTH: 19
<212> TYPE: DNA
<213> ORGANISM: Artificial Sequence
<220> FEATURE:
<223> OTHER INFORMATION: primer

<400> SEQUENCE: 19
aggcaatcct ccaagaacc                                                    19

<210> SEQ ID NO 20
<211> LENGTH: 19
<212> TYPE: DNA
<213> ORGANISM: Artificial Sequence
<220> FEATURE:
<223> OTHER INFORMATION: primer

<400> SEQUENCE: 20
tgaaagtcca gcaccttgg                                                    19

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
caacctgcag attcgagaaa                                                   20
```

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
gtcctgcctc acatcacatc                                                    20

<210> SEQ ID NO 23
<211> LENGTH: 21
<212> TYPE: DNA
<213> ORGANISM: Artificial Sequence
<220> FEATURE:
<223> OTHER INFORMATION: primer

<400> SEQUENCE: 23
tggttacatg agccccact a                                                   21

<210> SEQ ID NO 24
<211> LENGTH: 23
<212> TYPE: DNA
<213> ORGANISM: Artificial Sequence
<220> FEATURE:
<223> OTHER INFORMATION: primer

<400> SEQUENCE: 24
gaatcggaga tggatcgtaa tgg                                                23

<210> SEQ ID NO 25
<211> LENGTH: 20
<212> TYPE: DNA
<213> ORGANISM: Artificial Sequence
<220> FEATURE:
<223> OTHER INFORMATION: primer

<400> SEQUENCE: 25
gggcgcgtca taaaaagcac                                                    20

<210> SEQ ID NO 26
<211> LENGTH: 20
<212> TYPE: DNA
<213> ORGANISM: Artificial Sequence
<220> FEATURE:
<223> OTHER INFORMATION: primer

<400> SEQUENCE: 26
tgaacggggt gtagtggatg                                                    20

<210> SEQ ID NO 27
<211> LENGTH: 23
<212> TYPE: DNA
<213> ORGANISM: Artificial Sequence
<220> FEATURE:
<223> OTHER INFORMATION: primer

<400> SEQUENCE: 27
cgctcagaca cccttcagat aac                                                23

<210> SEQ ID NO 28
<211> LENGTH: 23
<212> TYPE: DNA
<213> ORGANISM: Artificial Sequence
<220> FEATURE:
<223> OTHER INFORMATION: primer

```
<400> SEQUENCE: 28
aaatcatcct cgatggtcac aac                                       23

<210> SEQ ID NO 29
<211> LENGTH: 19
<212> TYPE: DNA
<213> ORGANISM: Artificial Sequence
<220> FEATURE:
<223> OTHER INFORMATION: primer

<400> SEQUENCE: 29
tgcactccaa tcattcacg                                            19

<210> SEQ ID NO 30
<211> LENGTH: 20
<212> TYPE: DNA
<213> ORGANISM: Artificial Sequence
<220> FEATURE:
<223> OTHER INFORMATION: primer

<400> SEQUENCE: 30
gtgcgtgtta gaggtgatgg                                           20

<210> SEQ ID NO 31
<211> LENGTH: 21
<212> TYPE: DNA
<213> ORGANISM: Artificial Sequence
<220> FEATURE:
<223> OTHER INFORMATION: primer

<400> SEQUENCE: 31
ttcgggtttg tcacgtttga g                                         21

<210> SEQ ID NO 32
<211> LENGTH: 20
<212> TYPE: DNA
<213> ORGANISM: Artificial Sequence
<220> FEATURE:
<223> OTHER INFORMATION: primer

<400> SEQUENCE: 32
ggcctgtata actccggctg                                           20

<210> SEQ ID NO 33
<211> LENGTH: 21
<212> TYPE: DNA
<213> ORGANISM: Artificial Sequence
<220> FEATURE:
<223> OTHER INFORMATION: primer

<400> SEQUENCE: 33
cacctgtgcc agcctttctt a                                         21

<210> SEQ ID NO 34
<211> LENGTH: 20
<212> TYPE: DNA
<213> ORGANISM: Artificial Sequence
<220> FEATURE:
<223> OTHER INFORMATION: primer

<400> SEQUENCE: 34
tttcctccca ccctgtgtct                                           20

<210> SEQ ID NO 35
<211> LENGTH: 19
```

```
<212> TYPE: DNA
<213> ORGANISM: Artificial Sequence
<220> FEATURE:
<223> OTHER INFORMATION: primer

<400> SEQUENCE: 35
gtgagcaaga acatggccc                                              19

<210> SEQ ID NO 36
<211> LENGTH: 20
<212> TYPE: DNA
<213> ORGANISM: Artificial Sequence
<220> FEATURE:
<223> OTHER INFORMATION: primer

<400> SEQUENCE: 36
aaccagatct tgacctgcgt                                             20

<210> SEQ ID NO 37
<211> LENGTH: 20
<212> TYPE: DNA
<213> ORGANISM: Artificial Sequence
<220> FEATURE:
<223> OTHER INFORMATION: primer

<400> SEQUENCE: 37
gctgcgacga ctatcttccc                                             20

<210> SEQ ID NO 38
<211> LENGTH: 19
<212> TYPE: DNA
<213> ORGANISM: Artificial Sequence
<220> FEATURE:
<223> OTHER INFORMATION: primer

<400> SEQUENCE: 38
gcctcctagc ttgtcccca                                              19

<210> SEQ ID NO 39
<211> LENGTH: 21
<212> TYPE: DNA
<213> ORGANISM: Artificial Sequence
<220> FEATURE:
<223> OTHER INFORMATION: primer

<400> SEQUENCE: 39
aggtattacg agactggctc c                                           21

<210> SEQ ID NO 40
<211> LENGTH: 22
<212> TYPE: DNA
<213> ORGANISM: Artificial Sequence
<220> FEATURE:
<223> OTHER INFORMATION: primer

<400> SEQUENCE: 40
tcccgcttat actgggctat tt                                          22

<210> SEQ ID NO 41
<211> LENGTH: 20
<212> TYPE: DNA
<213> ORGANISM: Artificial Sequence
<220> FEATURE:
<223> OTHER INFORMATION: primer

<400> SEQUENCE: 41
```
ggatcgagac catgtgggac                                        20

<210> SEQ ID NO 42
<211> LENGTH: 20
<212> TYPE: DNA
<213> ORGANISM: Artificial Sequence
<220> FEATURE:
<223> OTHER INFORMATION: primer

<400> SEQUENCE: 42
gctgtgaggt tgtctgcact                                        20

<210> SEQ ID NO 43
<211> LENGTH: 21
<212> TYPE: DNA
<213> ORGANISM: Artificial Sequence
<220> FEATURE:
<223> OTHER INFORMATION: primer

<400> SEQUENCE: 43
agatgccaca ctcggagatc a                                      21

<210> SEQ ID NO 44
<211> LENGTH: 24
<212> TYPE: DNA
<213> ORGANISM: Artificial Sequence
<220> FEATURE:
<223> OTHER INFORMATION: primer

<400> SEQUENCE: 44
gagtacttgt cctccttgag cagc                                   24

<210> SEQ ID NO 45
<211> LENGTH: 20
<212> TYPE: DNA
<213> ORGANISM: Artificial Sequence
<220> FEATURE:
<223> OTHER INFORMATION: primer

<400> SEQUENCE: 45
agtctccaag cgacgaaaaa                                        20

<210> SEQ ID NO 46
<211> LENGTH: 20
<212> TYPE: DNA
<213> ORGANISM: Artificial Sequence
<220> FEATURE:
<223> OTHER INFORMATION: primer

<400> SEQUENCE: 46
gcaagaagcc tctccttgaa                                        20

<210> SEQ ID NO 47
<211> LENGTH: 20
<212> TYPE: DNA
<213> ORGANISM: Artificial Sequence
<220> FEATURE:
<223> OTHER INFORMATION: primer

<400> SEQUENCE: 47
ggcctttgga catctcttca                                        20

<210> SEQ ID NO 48
<211> LENGTH: 20
<212> TYPE: DNA
<213> ORGANISM: Artificial Sequence -continued

```
<220> FEATURE:
<223> OTHER INFORMATION: primer

<400> SEQUENCE: 48
atactcctca cgcaccttgc                                              20

<210> SEQ ID NO 49
<211> LENGTH: 21
<212> TYPE: DNA
<213> ORGANISM: Artificial Sequence
<220> FEATURE:
<223> OTHER INFORMATION: primer

<400> SEQUENCE: 49
agaactttgc cgttgaagct g                                            21

<210> SEQ ID NO 50
<211> LENGTH: 23
<212> TYPE: DNA
<213> ORGANISM: Artificial Sequence
<220> FEATURE:
<223> OTHER INFORMATION: primer

<400> SEQUENCE: 50
ccagagggag tgaatccaga tta                                          23

<210> SEQ ID NO 51
<211> LENGTH: 20
<212> TYPE: DNA
<213> ORGANISM: Artificial Sequence
<220> FEATURE:
<223> OTHER INFORMATION: primer

<400> SEQUENCE: 51
gtcagtggtg gacctgacct                                              20

<210> SEQ ID NO 52
<211> LENGTH: 20
<212> TYPE: DNA
<213> ORGANISM: Artificial Sequence
<220> FEATURE:
<223> OTHER INFORMATION: primer

<400> SEQUENCE: 52
caccaccctg ttgctgtagc                                              20
```

METHOD FOR DIFFERENTIATION OF NEURAL STEM CELLS, NEURONS AND GABAERGIC NEURONS FROM MESENCHYMAL STEM CELLS

CROSS REFERENCE TO RELATED APPLICATION

The present application claims priority to Korean Patent Application No. 10-2016-0044968, filed Apr. 12, 2016, the entire contents of which is incorporated herein for all purposes by this reference.

BACKGROUND

1. Field of the Invention

The present invention relates to a composition and a method for differentiation of neural stem cells, neurons and Gamma-aminobutyric acid (GABAergic) neurons from mesenchymal stem cells.

2. Description of the Related Art

There is as yet no obvious and reliable treatment method of nerve injury and neurodegenerative disease, thus still remaining an unsettled problem to clinicians and scientists. The stem cell has self-renewal ability and capacity to be differentiated into different systematic cells, and is considered as an effective source for cell treatment. Embryonic stem cells (ESCs) and induced pluripotent stem cells (iPSCs) are strong candidates applicable to regeneration therapeutics, and useful for biomedical applications such as diverse metabolic disease, genetic diseases, degenerative disease, or the like. However, due to some problems in terms of bioethics related to ESCs; as well as safety associated with foreign cell reprogramming factors possibly activating a carcinogenic pathway, and technical problems such as a low reprogramming process and low efficiency, etc. related to iPSCs, clinical application of ESCs and iPSCs is still faced with difficulties.

In a case of mature mesenchymal stem cells, these have some advantages such as self-suitability, high yield, high renewal ability, or the like, and therefore, being in the spotlight as a source more suitable for regenerative medicine.

Although a variety of efforts to differentiate mature mesenchymal stem cells into neural stem cells, neurons or GABAergic neurons have been conducted, an optimum differentiation protocol identified in functional and/or morphological aspects has not yet been disclosed.

Therefore, the present inventors have established the optimum protocol to differentiate mesenchymal stem cells into neural stem cells, neurons and GABAergic neurons using a small molecule inhibitor without gene manipulation, and therefore, the present invention has been completed on the basis of the established optimum protocol.

SUMMARY

An aspect of the present invention is to provide a composition for differentiation of neural stem cells from mesenchymal stem cells without gene manipulation.

Another aspect of the present invention is to provide a method for differentiation of neural stem cells, neurons and GABAergic neurons from mesenchymal stem cells without gene manipulation.

The above aspects of the present invention will be achieved by one or more of the following characteristics:

(1) A method for differentiation of neural stem cells from mesenchymal stem cells, including: 1) culturing the mesenchymal stem cells in a medium containing SB431542, Noggin and LDN193189.

(2) The method according to the above (1), wherein the mesenchymal stem cell is at least one selected from a group consisting of bone marrow-derived mesenchymal stem cells and adipose-derived mesenchymal stem cells (ADSC).

(3) The method according to the above (1), further including: 2) culturing the cells cultured in step 1) in a medium containing B27, N2 and ascorbic acid; and 3) culturing the cells cultured in step 2) in a medium containing epidermal growth factor (EGF) and basic fibroblast growth factor (bFGF).

(4) The method according to the above (1), wherein the SB431542 is included in an amount of 1 to 200 μM, the Noggin is included in an amount of 0.01 to 1 μg/ml, and the LDN193189 is included in an amount of 0.1 to 20 μM.

(5) The method according to the above (1), wherein the SB431542 is included in an amount of 5 to 20 μM, the Noggin is included in an amount of 0.05 to 0.2 μg/ml, and the LDN193189 is included in an amount of 0.1 to 1.0 μM.

(6) The method according to the above (1), wherein the culturing in step 1) is conducted for 4 to 12 days.

(7) The method according to the above (2), wherein the culturing in step 2) is conducted for 3 to 10 days; and the culturing in step 3) is conducted for 3 to 10 days.

(8) A method for differentiation of GABAergic neurons from mesenchymal stem cells, including: 1) culturing the mesenchymal stem cells in a medium containing SB431542, Noggin and LDN193189.

(9) The method according to the above (8), further including: 2) culturing the cells cultured in step 1) in a medium containing B27, N2 and ascorbic acid; 3) culturing the cells cultured in step 2) in a medium containing purmorphamine and BDNF to differentiate the cells into neurons; and 4) culturing the neurons differentiated in step 3) in a medium containing dbcAMP and BDNF.

(10) The method according to the above (8), wherein the mesenchymal stem cell is at least one selected from a group consisting of bone marrow-derived mesenchymal stem cells and adipose-derived mesenchymal stem cells.

(11) The method according to the above (8), wherein the SB431542 is included in an amount of 1 to 200 μM, the Noggin is included in an amount of 0.01 to 1 μg/ml, and the LDN193189 is included in an amount of 0.1 to 20 μM, in step 1).

(12) The method according to the above (8), wherein the purmorphamine is included in an amount of 1 to 50 μM, and the BDNF is included in an amount of 1 to 500 ng/ml, in step 3).

(13) The method according to the above (8), wherein the dbcAMP is included in an amount of 0.01 to 1 mM, and the BDNF is included in an amount of 1 to 500 ng/ml, in step 4).

(14) The method according to the above (8), wherein the culturing in step 1) is conducted for 4 to 12 days.

(15) The method according to the above (9), wherein the culturing in step 2) is conducted for 3 to 10 days; the culturing in step 3) is conducted for 7 to 16 days; and the culturing in step 4) is conducted for 10 to 40 days.

(16) A composition for cell differentiation, including SB431542, Noggin and LDN193189.

(17) The composition according to the above (16), further including B27, N2, ascorbic acid, an epidermal growth factor (EGF) and a basic fibroblast growth factor (bFGF).

(18) The composition according to the above (16), further including purmorphamine, dibutyryl cyclic AMP (dbcAMP) and BDNF.

(19) The composition according to the above (16), wherein the SB431542 is included in an amount of 1 to 200 μM, the Noggin is included in an amount of 0.01 to 1 μg/ml, and the LDN193189 is included in an amount of 0.1 to 20 μM.

(20) The composition according to the above (16), wherein the purmorphamine is included in an amount of 1 to 50 μM, the dbcAMP is included in an amount of 0.01 to 1 mM, and the BDNF is included in an amount of 1 to 500 ng/ml.

According to embodiments of the present invention, the composition for differentiation of neural stem cells may differentiate mesenchymal stem cells into neural stem cells, neurons and GABAergic neurons without gene manipulation.

The method according to an embodiment of the present invention may differentiate mesenchymal stem cells into neural stem cells, neurons and GABAergic neurons at a high transformation rate.

BRIEF DESCRIPTION OF THE DRAWINGS

The above and other aspects, features and other advantages of the present invention will be more clearly understood from the following detailed description taken in conjunction with the accompanying drawings, in which:

FIG. 1A: Diagram illustrating a process of inducing differentiation of neural stem cells from adipose-derived mesenchymal stem cells.

FIG. 1B: Diagram illustrating Bright-field images of hADSCs in culture. Scale bar: 100 μm.

FIG. 1C: Diagrams illustrating analyzed results of characteristics of induced neural stem cell through real time PCR. The longitudinal axis represents a relative amount of gene expression.

*$P<0.05$, $P<0.01$, and *$P<0.001$ significance probabilities are values compared to adipose-derived mesenchymal stem cell, while $^\dagger P<0.05$, $^{\dagger\dagger}P<0.01$, and $^{\dagger\dagger\dagger}P<0.001$ significance probabilities are values compared to a group without treatment using the small molecule inhibitor.

Figure 1A:
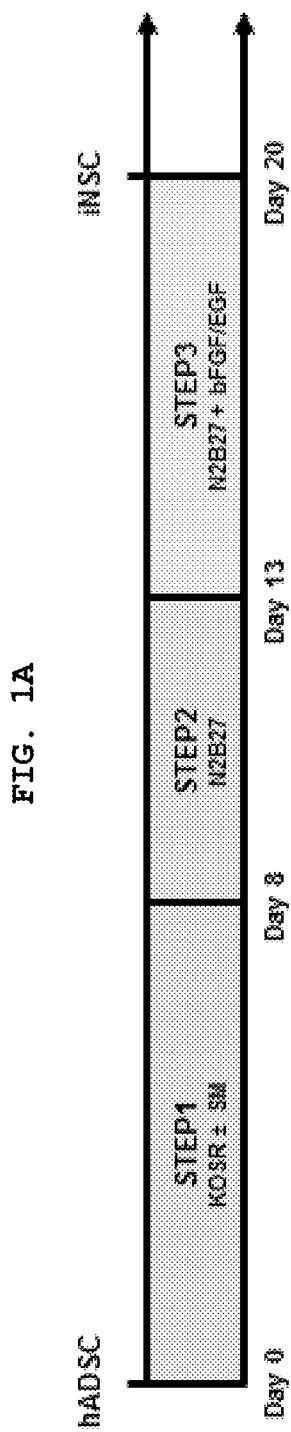
FIGS. 1A to 1D are diagrams illustrating Induction of neural stem cell-like cells (iNSCs) from human adipose-derived mesenchymal stem cells (hADSCs) using small molecules (SMs)
Figure 1B:
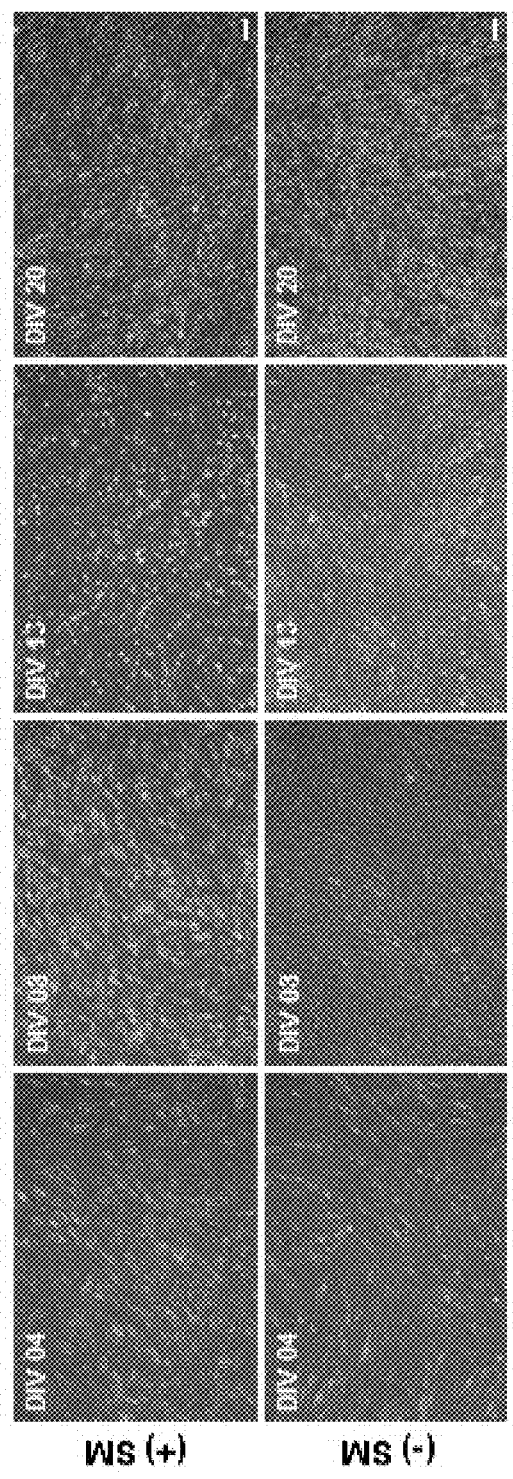
Figure 1C:
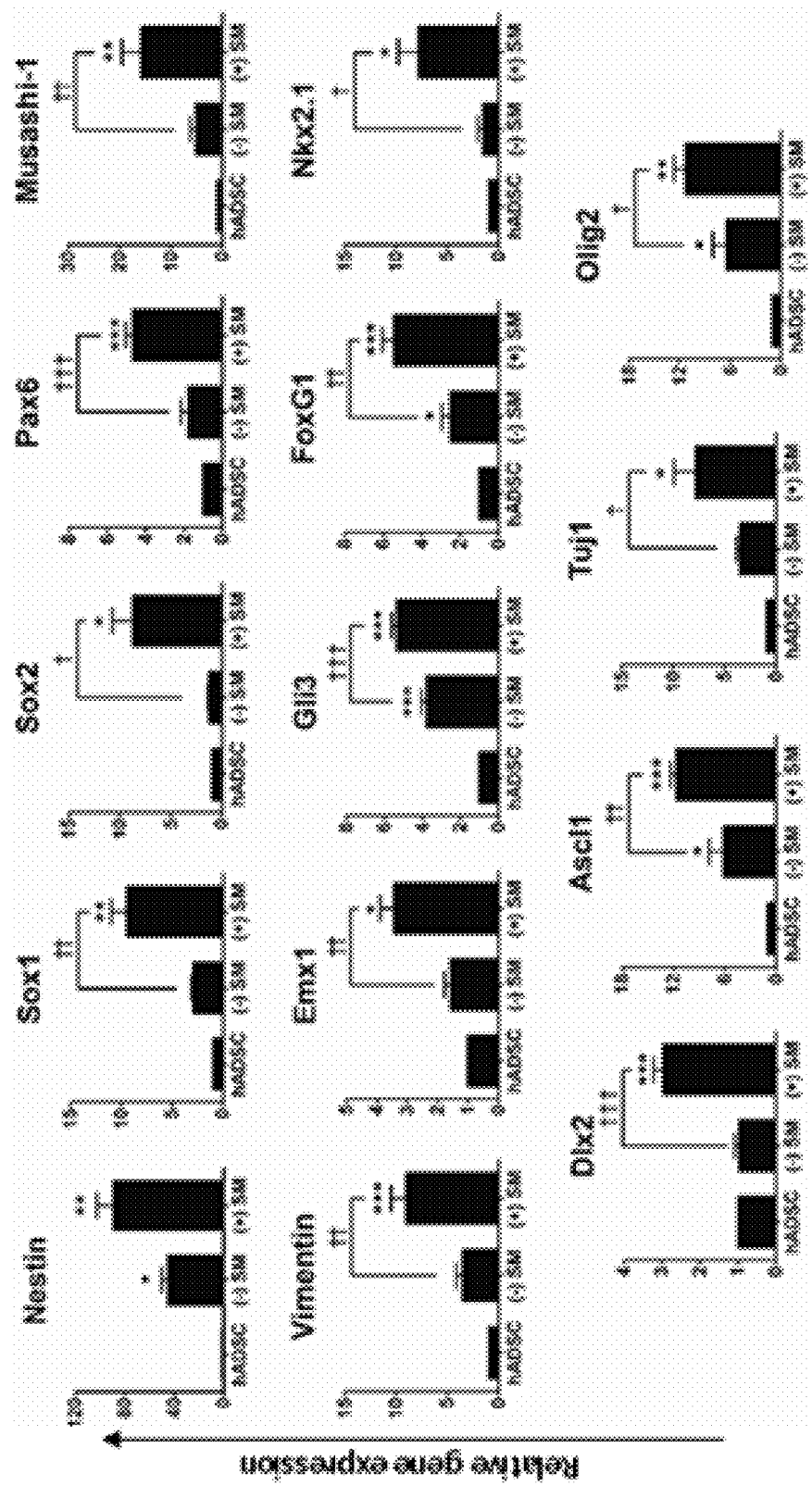
Figure 1D:
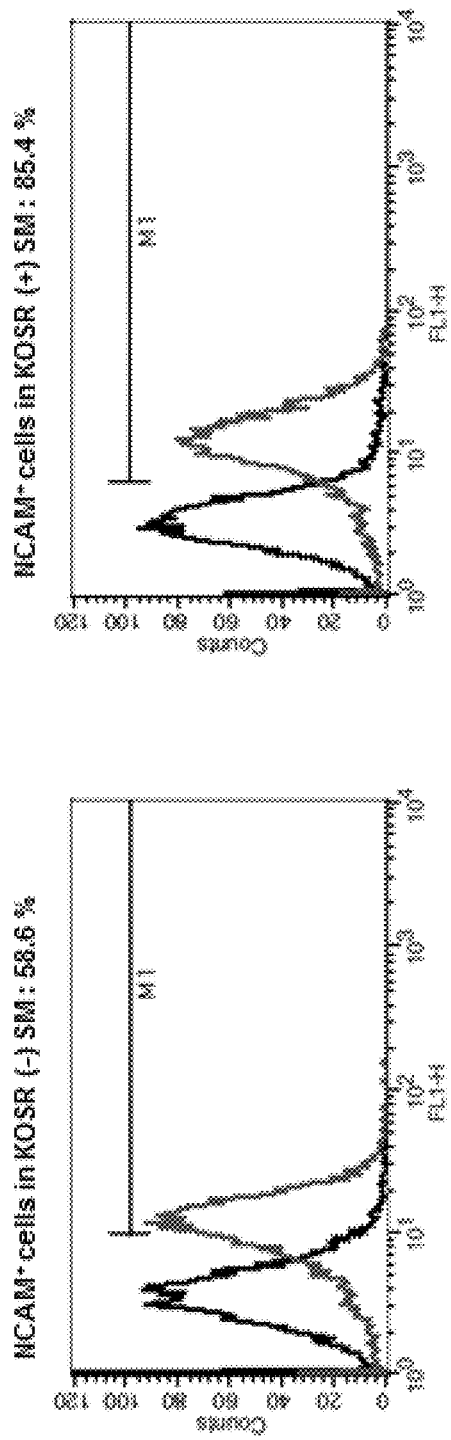

FIG. 1D: Diagrams illustrating flow cytometry analysis of neural cell adhesion molecule (NCAM)-positive cells after NSC induction with (+) or without (−) SMs using a fluorescent assisted cell sorting (FACS) caliber.

Figure 2A:
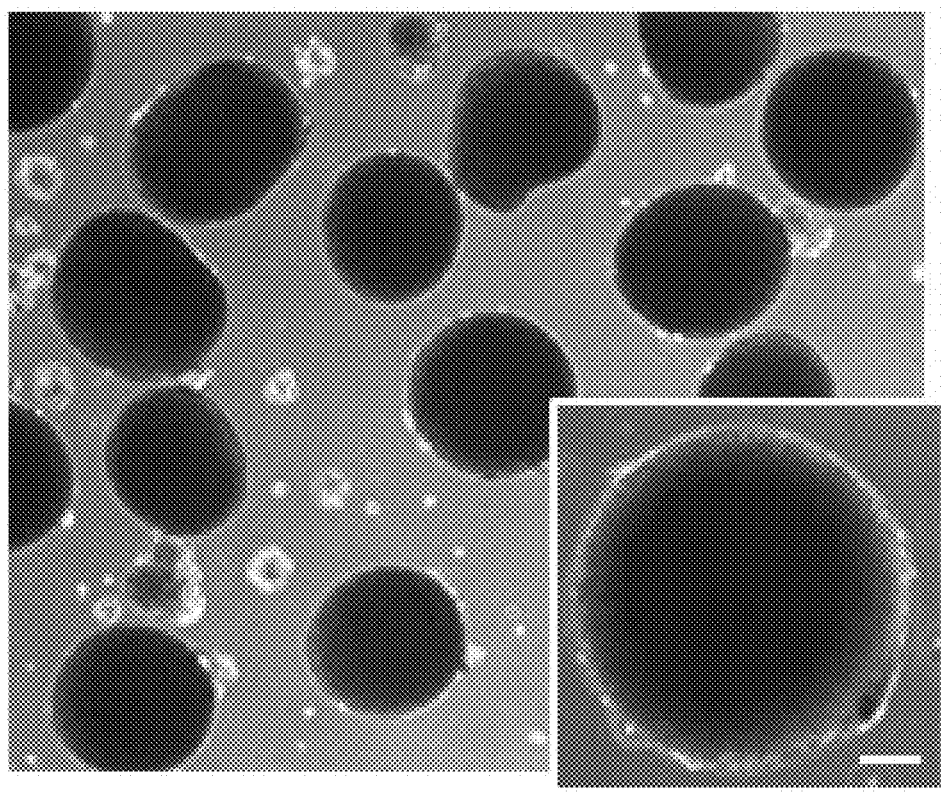

FIGS. 2A to 2D are diagrams illustrating characteristics of induced neural stem cell (iNSCs) derived from human adipose-derived stem cells (hADSCs) by the optimized induction method:

FIG. 2A: Diagrams illustrating neurosphere formation of iNSCs in suspension at DIV 4 after passage. Scale bar: 100 μm.

Figure 2B:
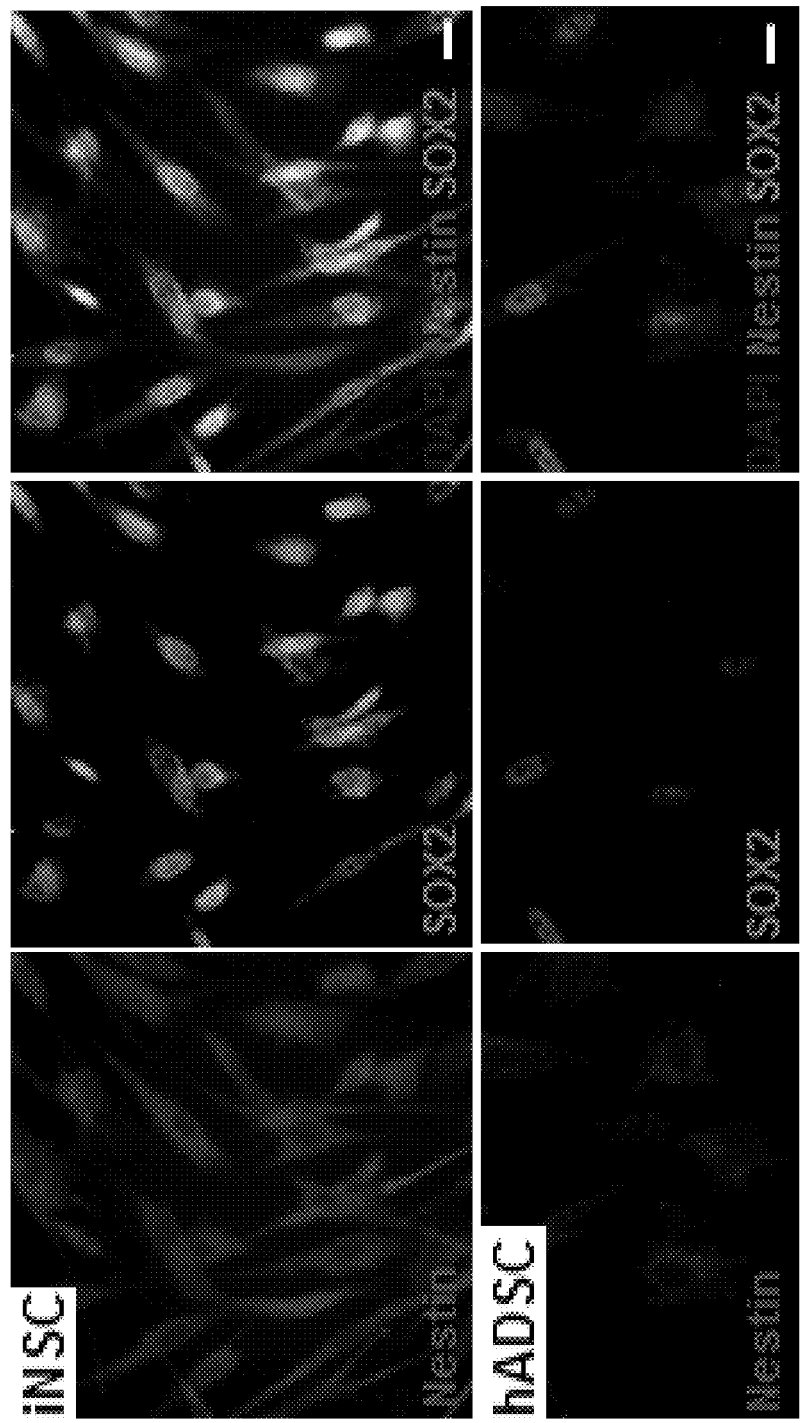

FIG. 2B: Diagrams illustrating detection of induced neural stem cell expressing both of Nestin and Sox2 through fluorescent immune cell staining.

Figure 2C:
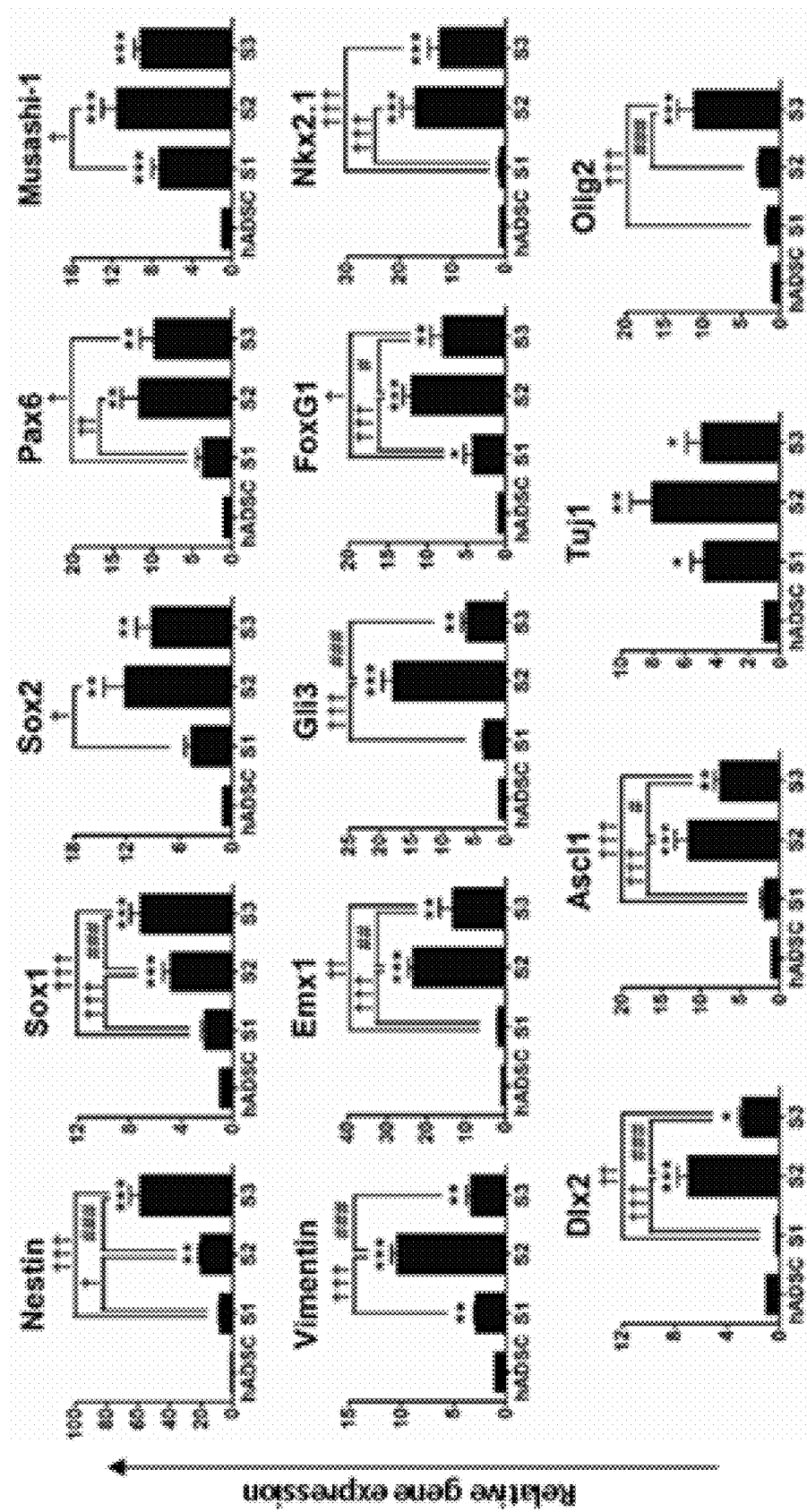

FIG. 2C: Diagrams illustrating changes of expression of neural stem cell and initial neuron molecular markers (Sox1, Sox2, Nestin, Musashi-1, FoxG1, Nkx2.1, Pax6, Gli3, Vimentin, Tuj1 and Emx1) along a process of cross-differentiation of neural stem cells through real time PCR. The longitudinal axis represents a relative amount of gene expression.

*$P<0.05$, $P<0.01$, and *$P<0.001$ significance probabilities are values compared to human adipose-derived mesenchymal stem cell.

$^\dagger P<0.05$, $^{\dagger\dagger}P<0.01$, and $^{\dagger\dagger\dagger}P<0.001$ significance probabilities are values compared to cells cultured in a medium containing SB431542, Noggin and LDN193189, while $^\#P<0.05$ significance probability is a value compared to cells cultured in a medium containing B27, N2 and ascorbic acid.

Figure 2D:
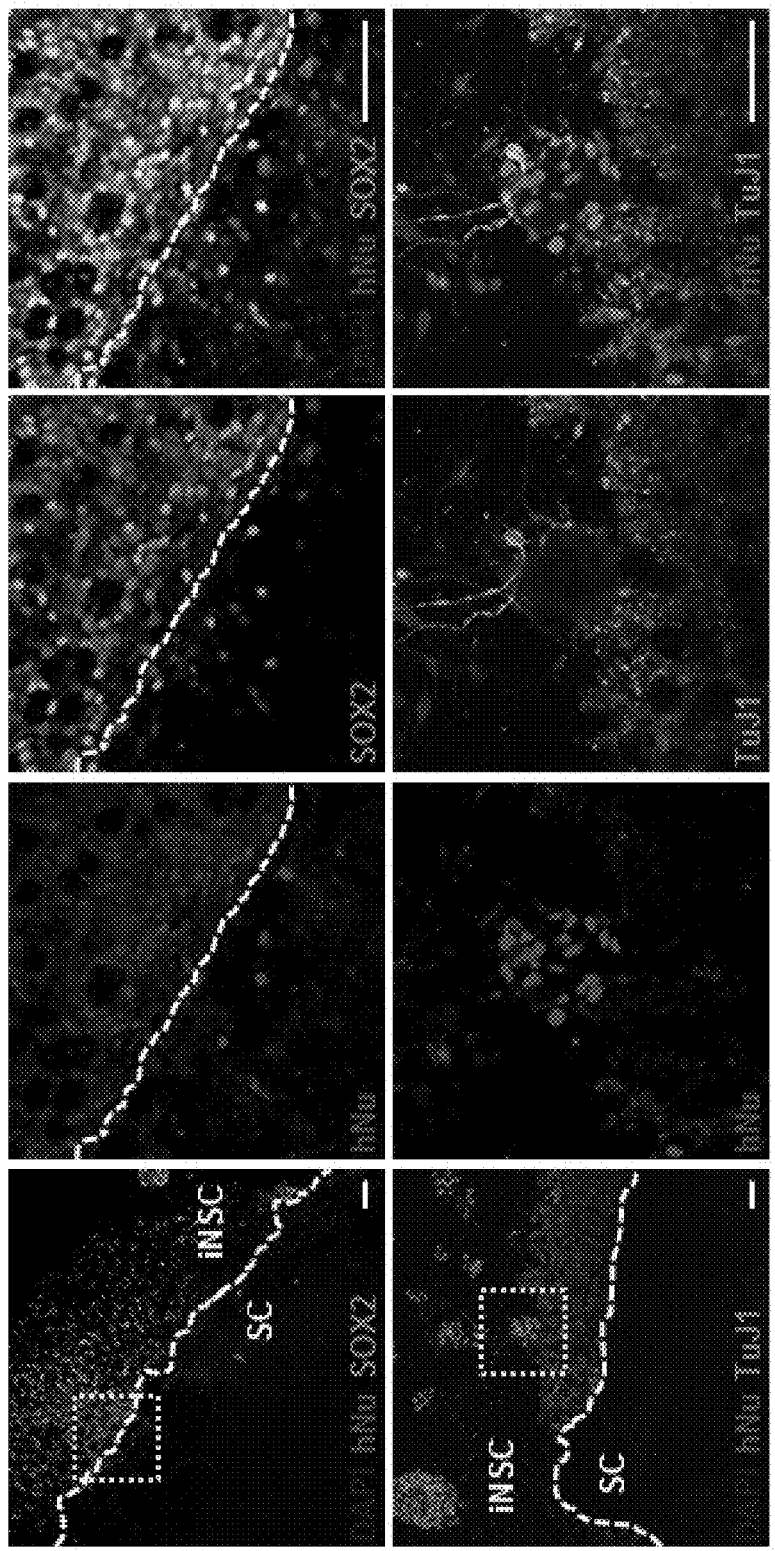

FIG. 2D: Diagrams illustrating transplantation of iNSCs on the ventral horn of rat organotypic spinal cord slice. Scale bar: 100 μm.

Figure 3A:
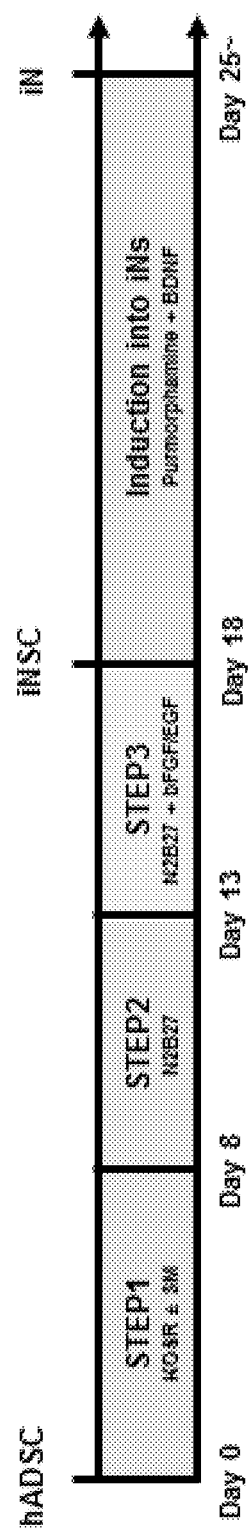
Figure 3B:
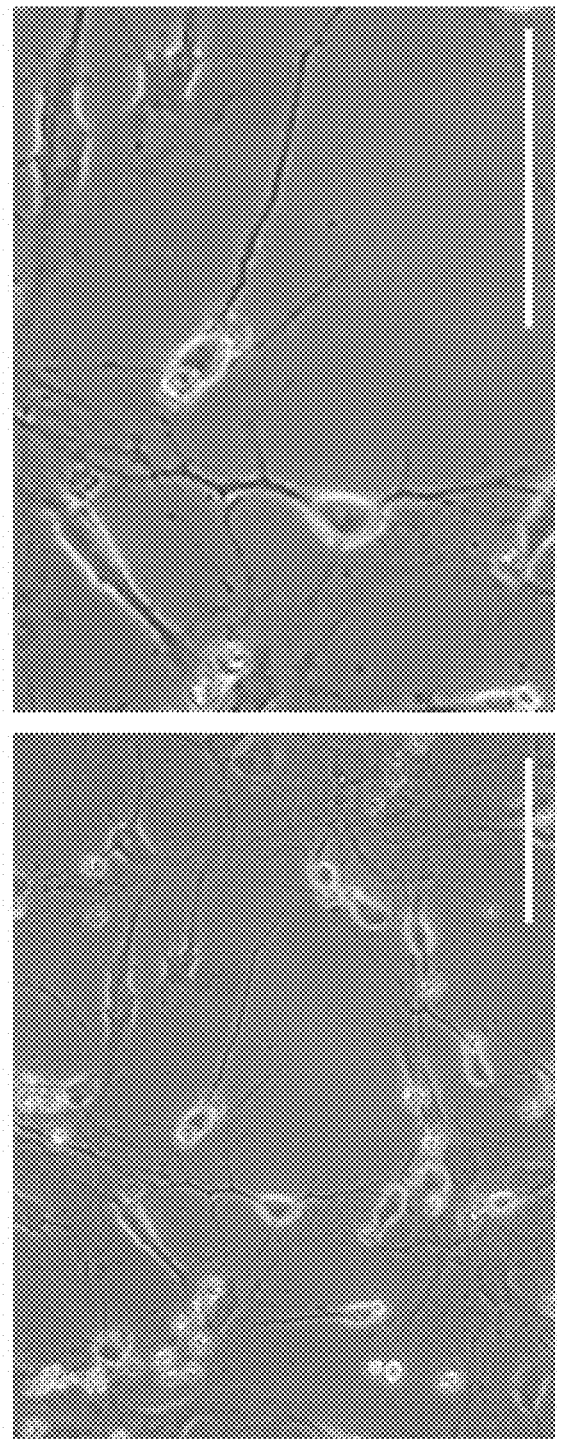
Figure 3C:
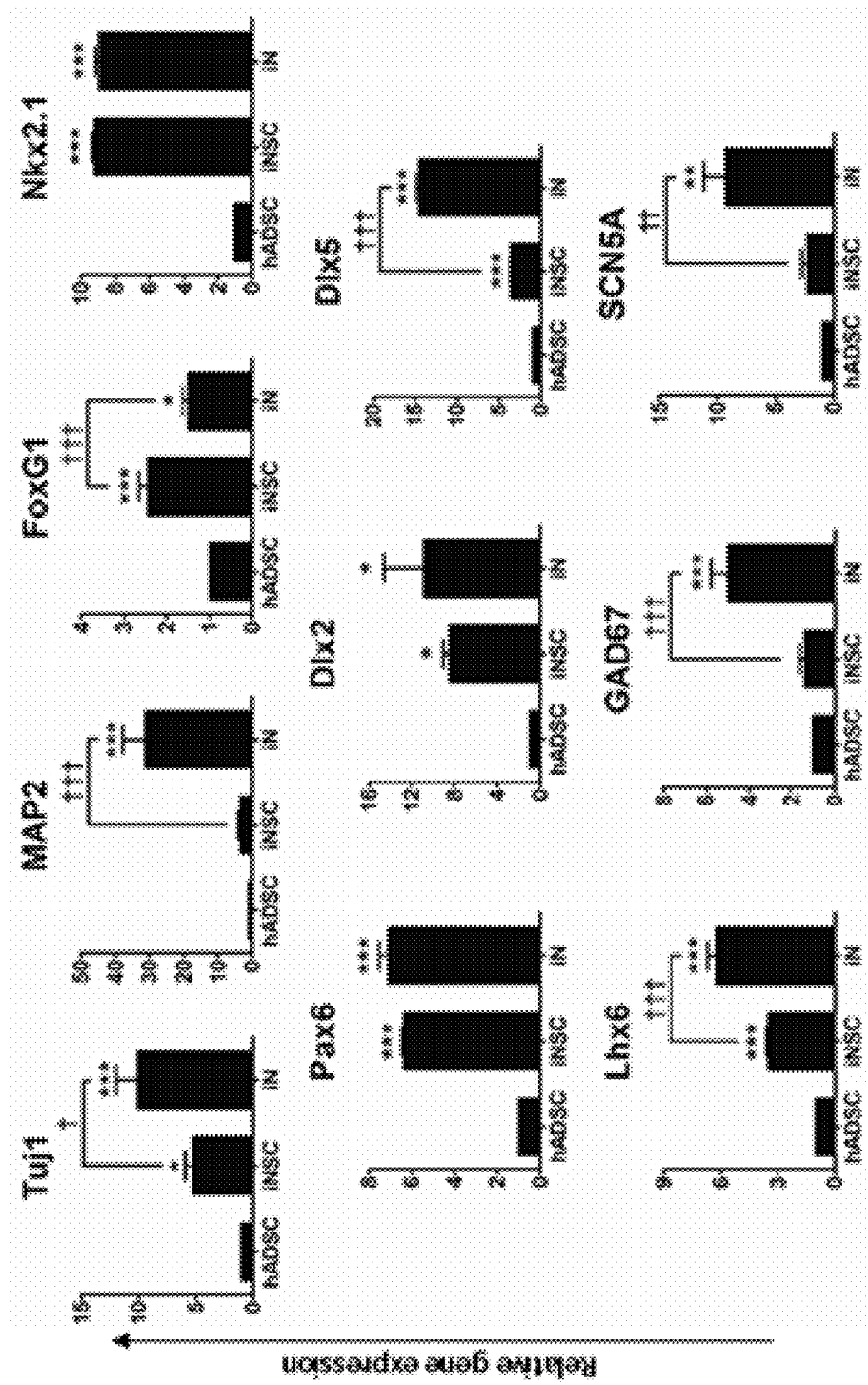

FIGS. 3A to 3C are diagrams illustrating Induction of iNSCs into neuron-like cells (iNs):

FIG. 3A: Diagram illustrating experiments in regard to differentiation of induced neurons from adipose-derived mesenchymal stem cells.

FIG. 3B: Diagrams illustrating a morphology of induced neurons substantially identical to mature neurons. Scale bar: 100 μm.

FIG. 3C: iNSC (induced neural stem cells), iN (induced neurons)

*$P<0.05$, $P<0.01$, and *$P<0.001$ significance probabilities are values compared iN to adipose-derived mesenchymal stem cells, while $^\dagger P<0.05$, $^{\dagger\dagger}P<0.01$, and $^{\dagger\dagger\dagger}P<0.001$ significance probabilities are values compared iN to induced neural stem cells. ANOVA followed by post hoc Newman-Keuls test.

Figure 4A:
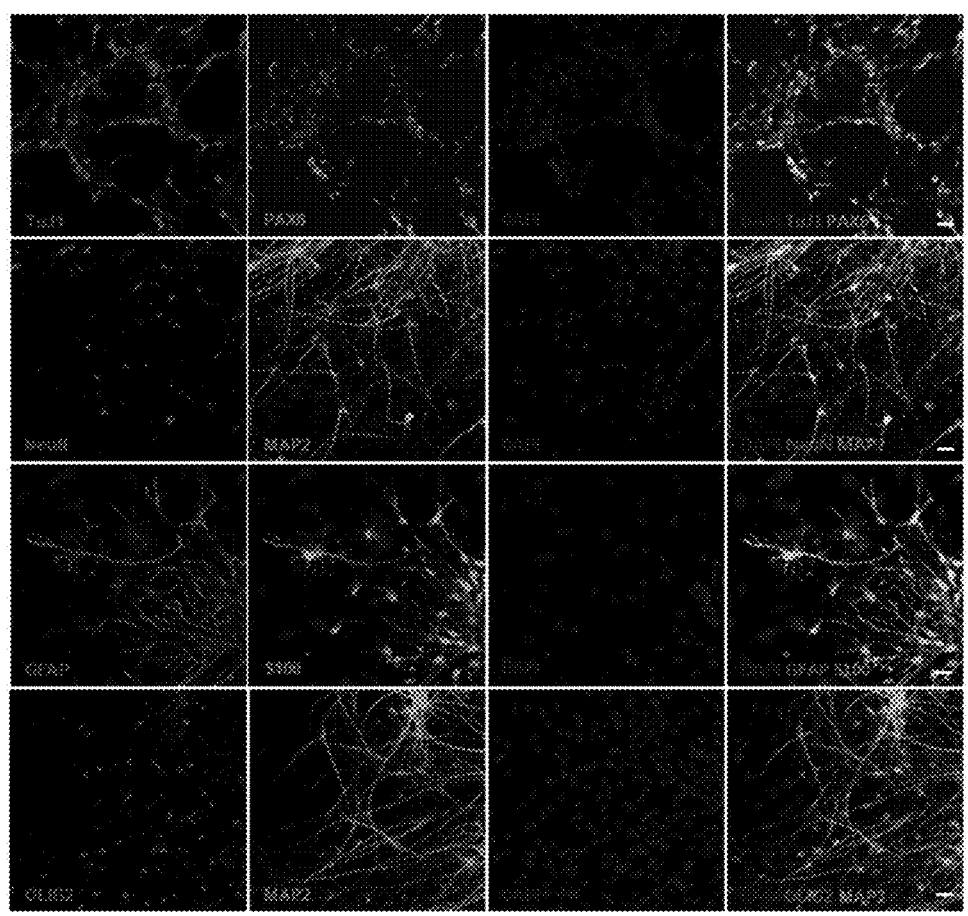
Figure 4C:
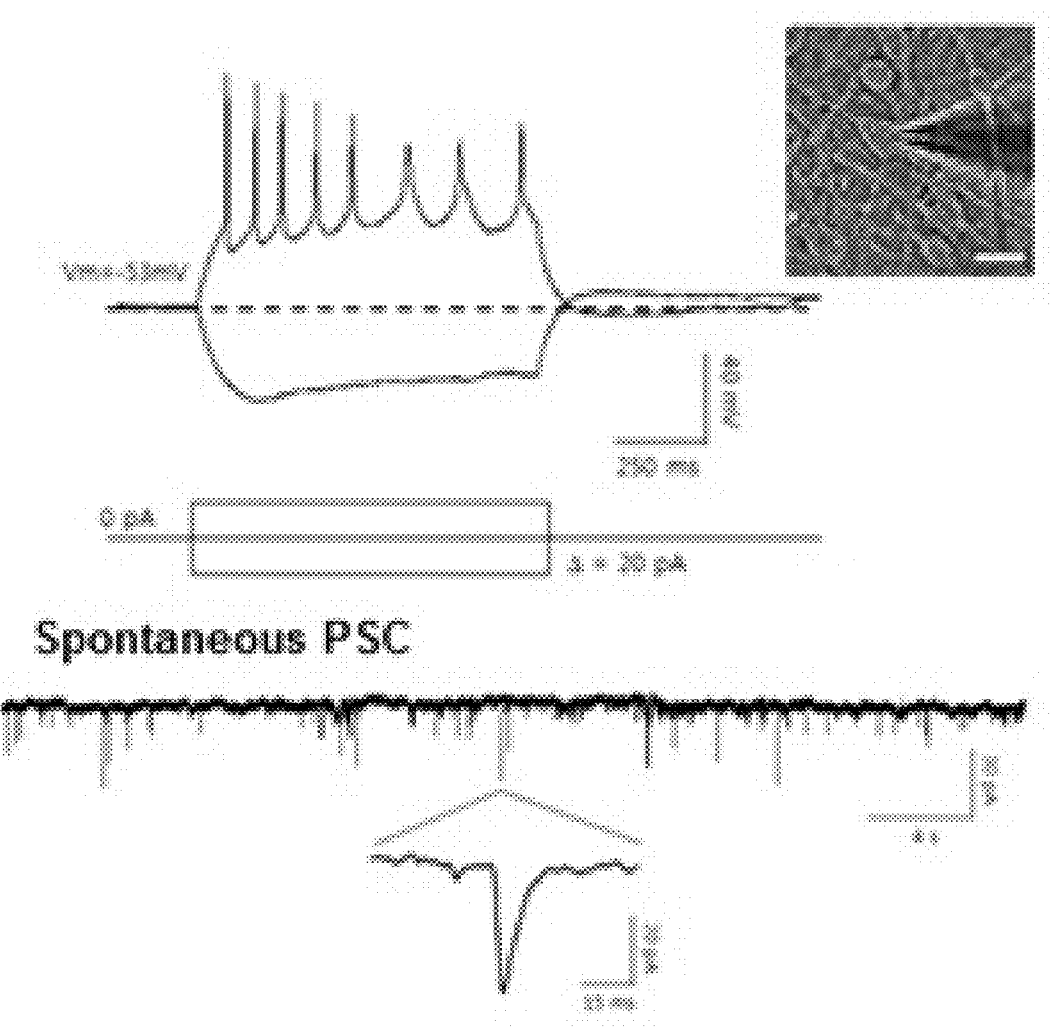

FIGS. 4A to 4C are diagrams illustrating characteristics of induced neurons derived from adipose-derived mesenchymal stem cells:

FIG. 4A: Scale Bar: 20 μm.

FIG. 4B: Calculating the number of the induced neurons expressing neuron precursor cell, neuron and/or glial cell ('neuroglia') molecular markers in at least three different regions. A percentage thereof indicates a rate of the number of the induced neurons expressing the corresponding molecular marker occupying in the induced neurons expressing DAPI, which corresponds to a total number of cells (mean value±standard error of the mean value).

FIG. 4C: Diagrams illustrating electrical and physiological record sample measured from the induced neuron having any typical morphology of neurons. Sample image and induction of action potential by current input are shown, and a current input protocol is indicated below the record of action potential. The record at the bottom part indicates a representative spontaneous synapse action obtained from the induced neurons in a fixed voltage clamp mode (−60 mV fixed), and the enlarged single current is represented below the continuously indicated record (Spontaneous PSC).

Figure 5A:
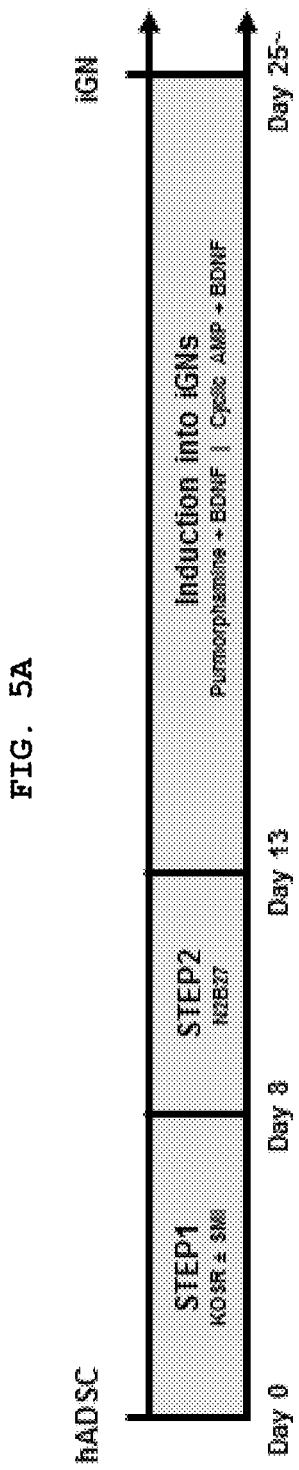

FIGS. 5A to 5D are diagrams illustrating optimization of cross-differentiation protocol from adipose-derived mesenchymal stem cells to GABAergic neurons:

FIG. 5A: Modified induction scheme of iGNs from hADSCs. The STEP3 of iNSC induction was skipped to expand the days for neuronal maturation and dbcAMP was added to prevent cell death of induced neurons.

Figure 5B:
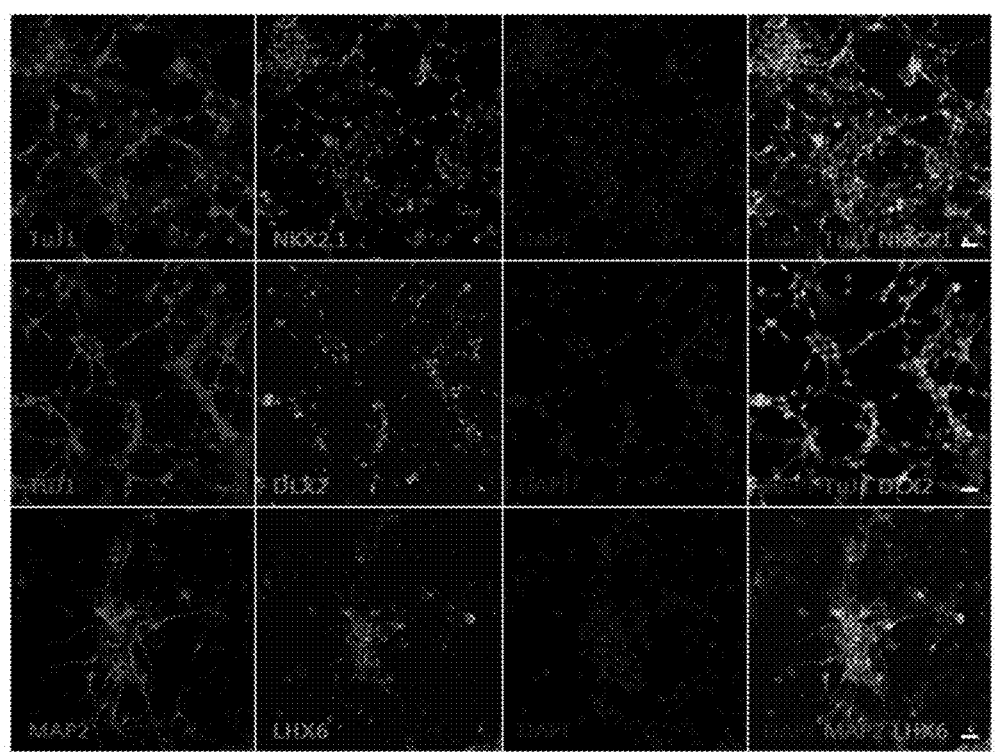

FIG. 5B: Scale bar: 20 μm.

FIG. 5C: Counting the number of the induced GABAergic neurons expressing medial ganglionic eminence (MGE) cell and neuron molecular markers in at least three regions. A percentage thereof indicates a rate of the number of the induced GABAergic neurons expressing the corresponding molecular marker occupying in the induced neurons expressing DAPI, which corresponds to a total number of cells (mean value±standard error of the mean value)

Figure 5D:
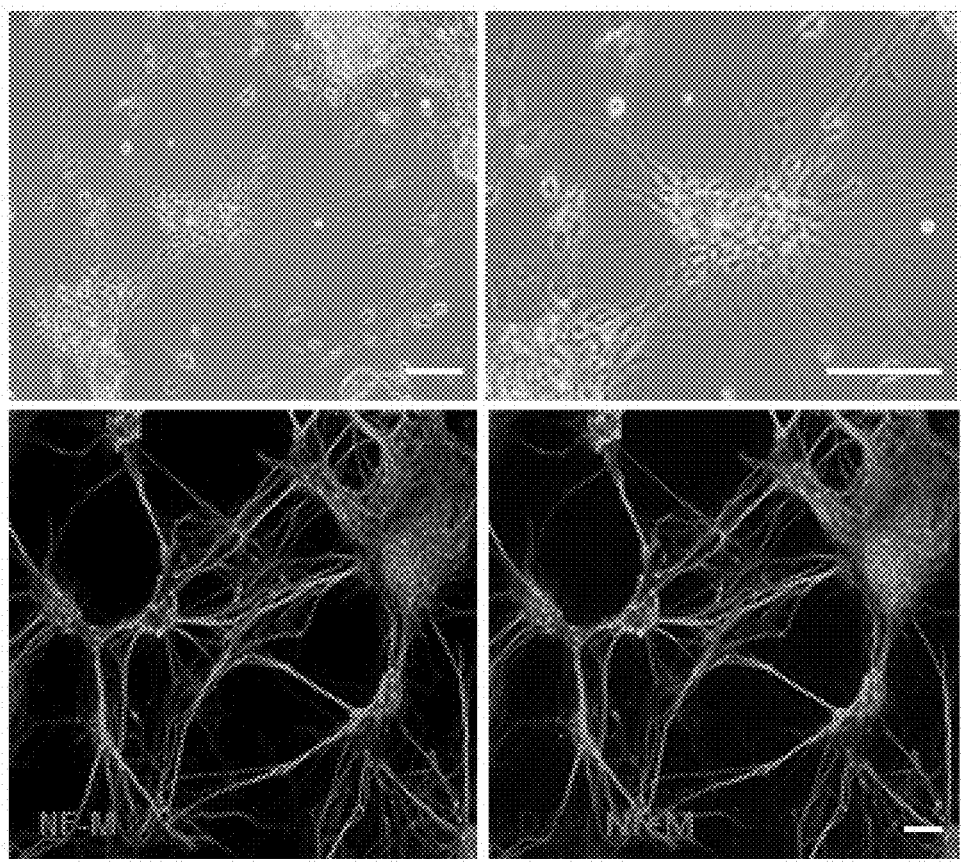

FIG. 5D: Scale bar: 100 μm.

Figure 6A:
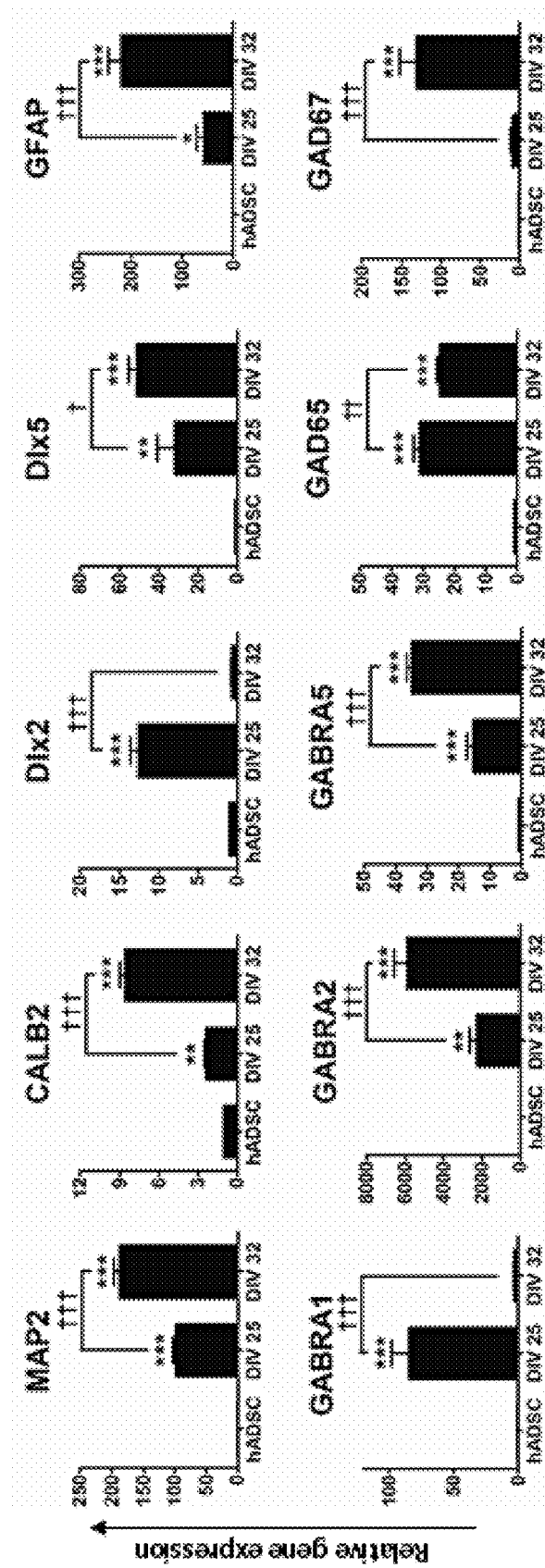

FIGS. 6A to 6D are diagrams illustrating functional characteristics of induced GABAergic neurons:

FIG. 6A: *P<0.05, P<0.01, and *P<0.001 significance probabilities are values compared induced GABAergic neurons to adipose-derived mesenchymal stem cell, while †P<0.05, ††P<0.01, and †††P<0.001 significance probabilities are values compared induced GABAergic neurons to induced GABAergic neurons on day 25 of tube culture. ANOVA followed by post hoc Newman-Keuls test.

Figure 6B:
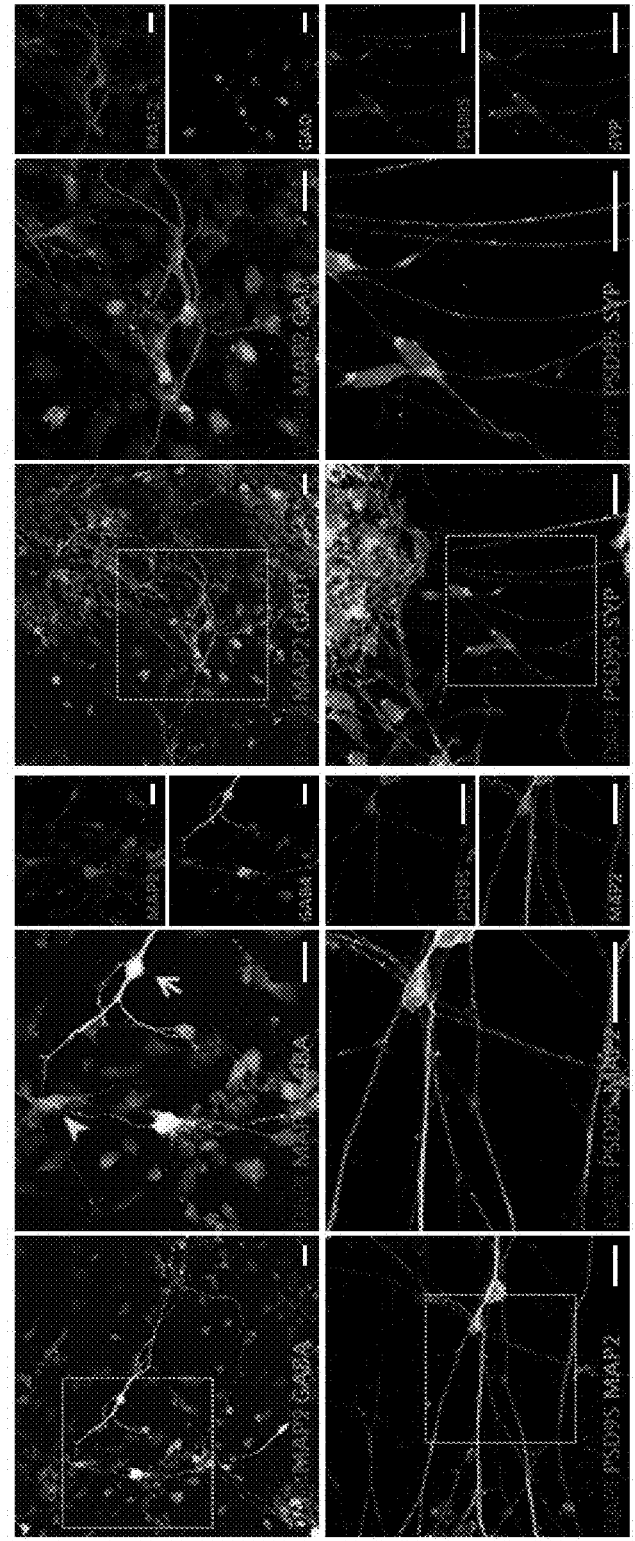

FIG. 6B: Scale bar: 20 μm.

FIG. 6C: Counting the number of the induced GABAergic neurons expressing GABAergic neuron molecular markers in at least three regions. A percentage thereof indicates a rate of the number of the induced GABAergic neurons expressing the corresponding molecular marker occupying in the induced GABAergic neurons expressing DAPI, which corresponds to a total number of cells (mean value±standard error of the mean value).

Figure 6D:
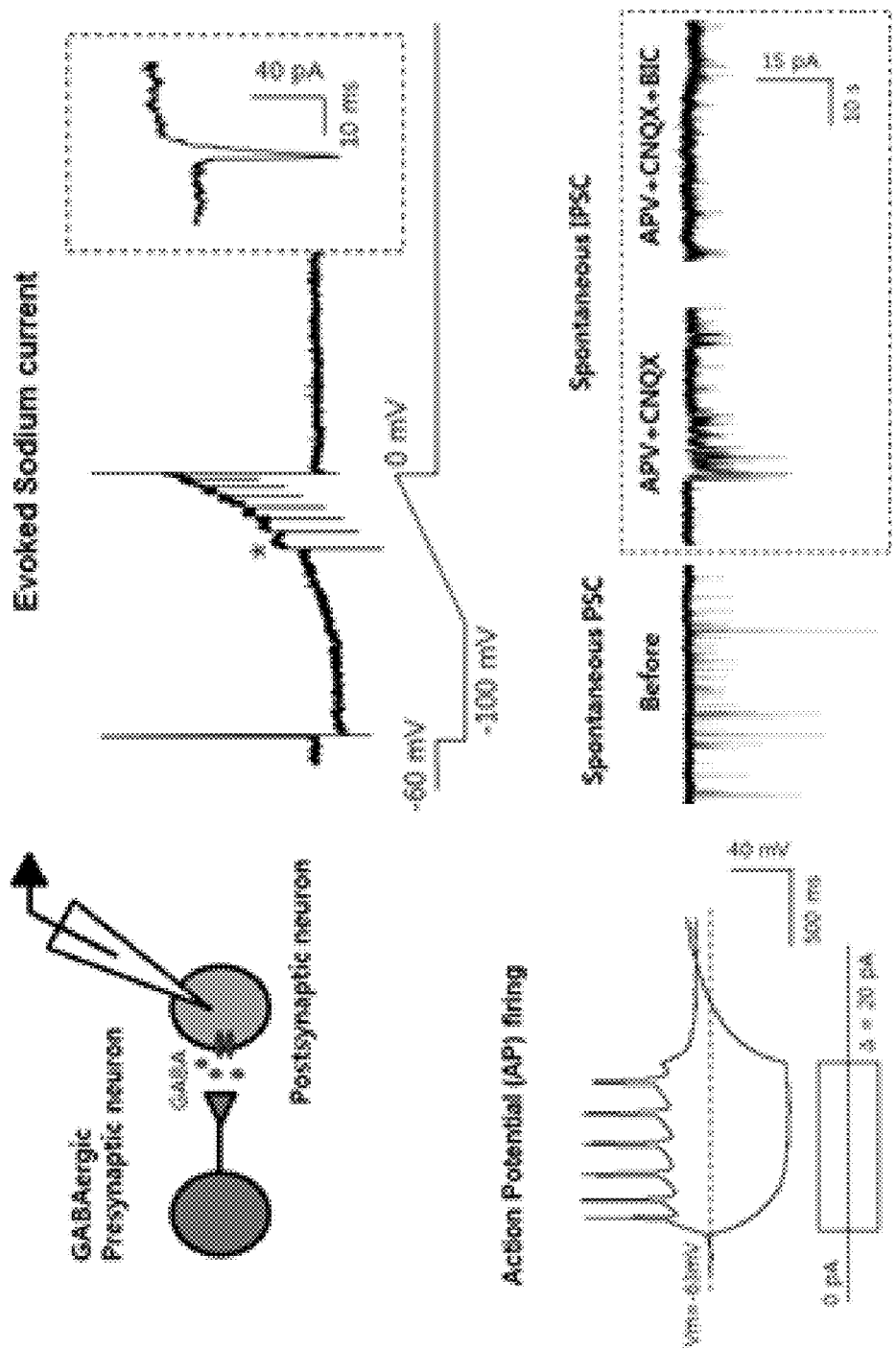

FIG. 6D: The top left side panel shows a record of expressing action potential of the induced GABAergic neurons recorded in a fixed current clamp mode. A current input protocol is indicated below the record of action potential.

At the top right side panel, it could be seen that a rapid current inflow is induced in the induced GABAergic neurons by applying a lamp protocol, while depolarizing the fixed voltage. The voltage was gradually increased from −100 mV to 0 mV for 1 second, and the dotted box shows the current indicated with asterisk in enlarged scale.

A schematic view of the design of experiments is illustrated at the bottom left side panel.

FIGS. 7A to 7D are diagrams illustrating microarray analysis of neural stem cells (iNSCs) and GABAergic neurons (iGNs) induced from human adipose-derived mesenchymal stem cells (hADSCs).

Figure 7A:
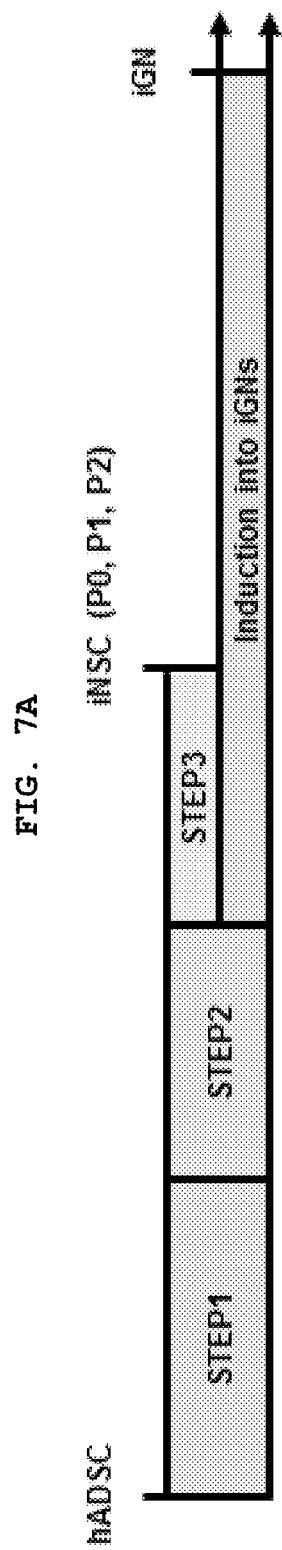

FIG. 7A: Diagrams illustrating schematics of samples for microarray analysis.

Figure 7B:
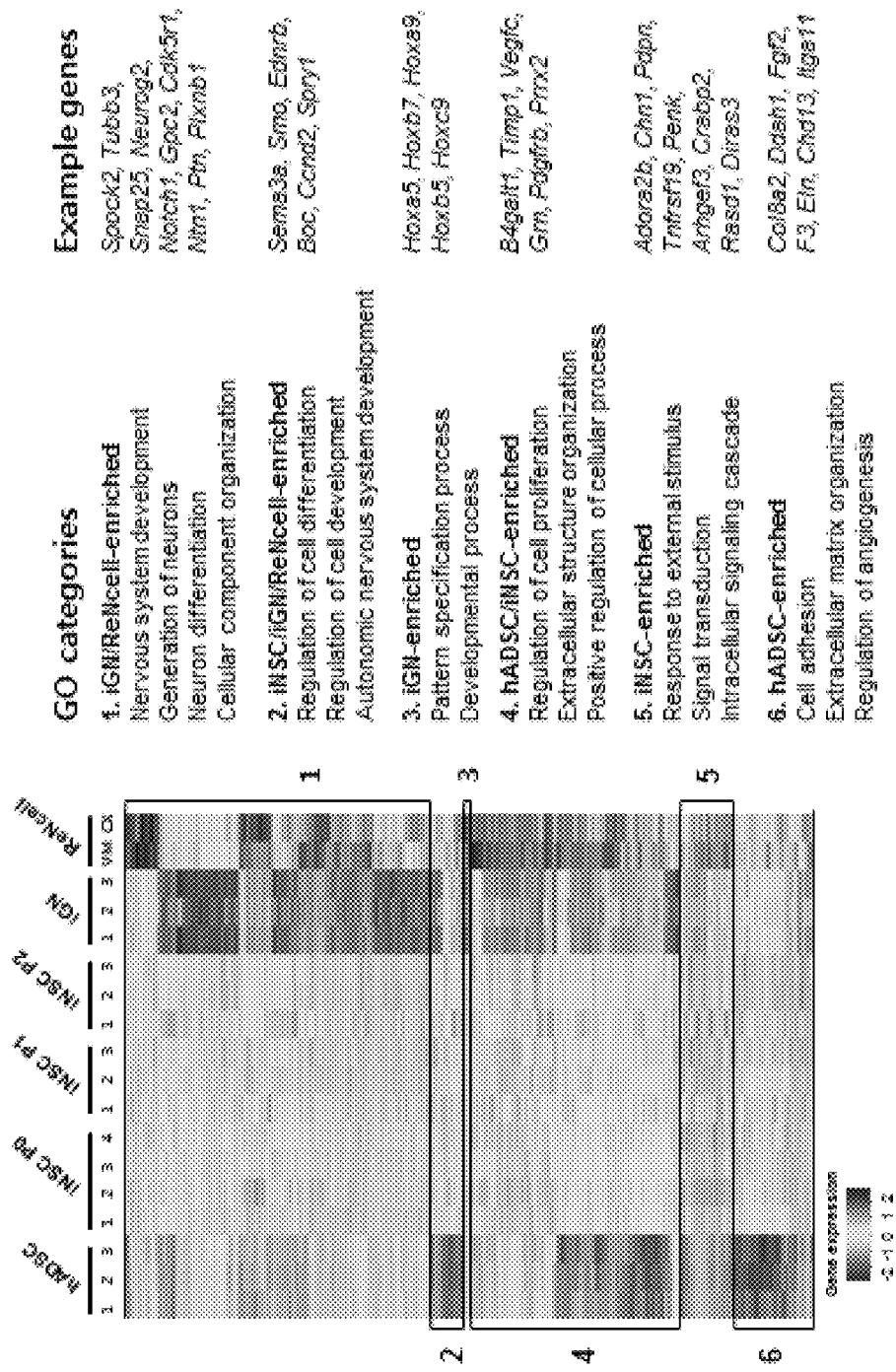

FIG. 7B: Diagrams illustrating heatmap for differentially expressed genes (P<0.005, Kruskall-Wallis test with Conover correction for multiple comparisons).

Figure 7C:
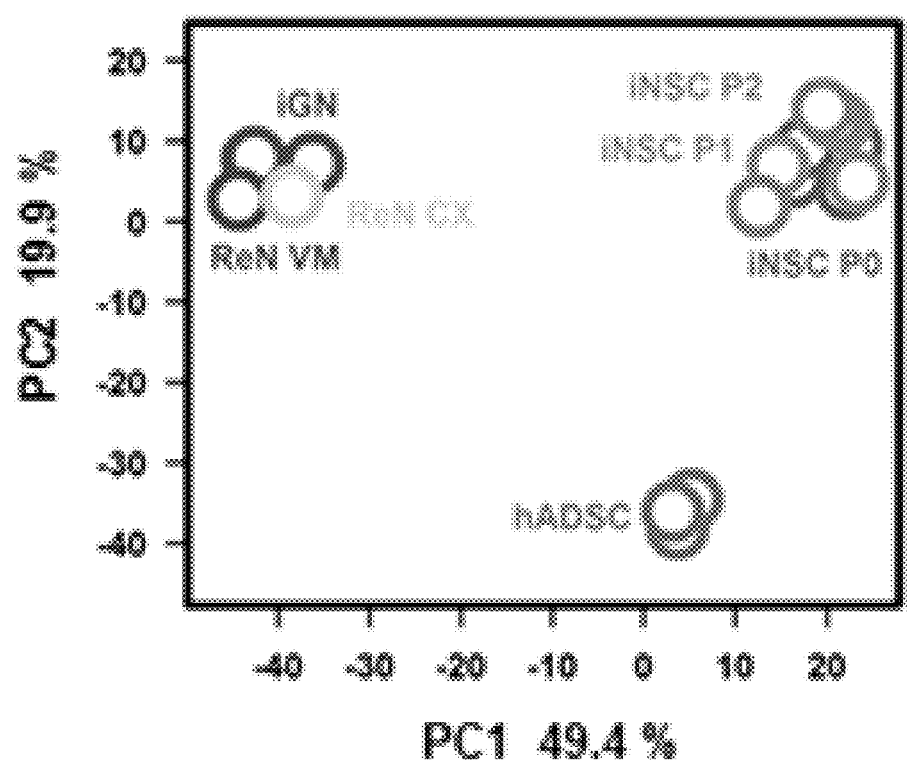

FIG. 7C: Diagrams illustrating multidimensional scaling of hADSCs, iNSCs, iGNs, ReN VM and CX samples.

Figure 7D:
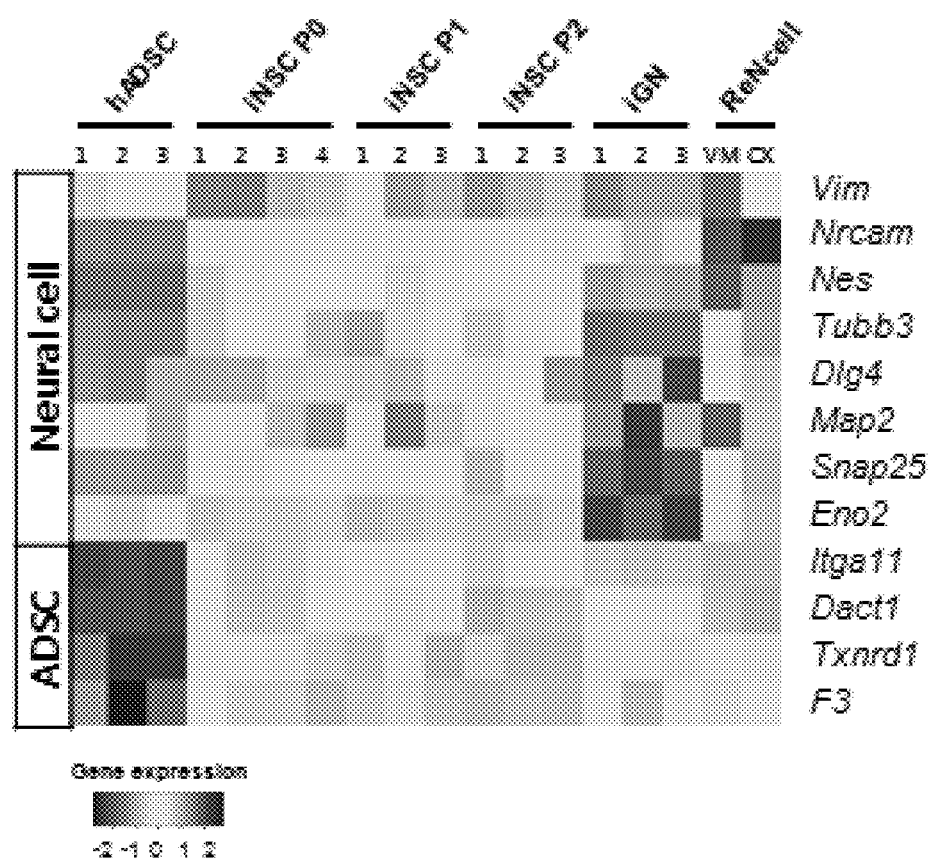

FIG. 7D: Diagrams illustrating heatmap representation of expression profiles of 8 neural cell- and 4 hADSC-enriched genes at each sample. The numbers above heatmap depict independent biological replicates of each group.

Figure 8:
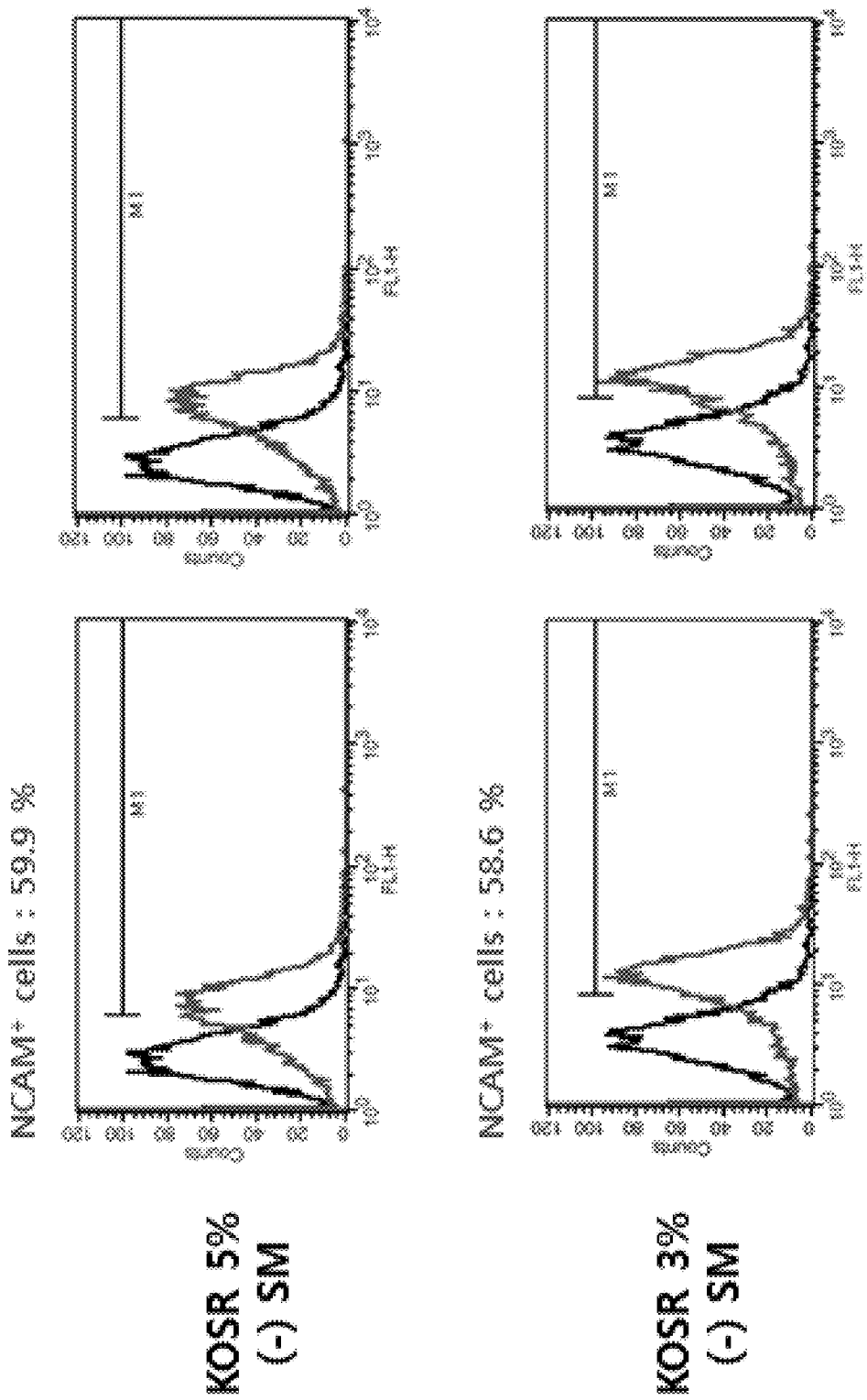

FIG. 8 is diagrams illustrating comparative analysis of NSC induction from hADSCs using different concentrations of knock-out serum (KOSR).

Figure 9:
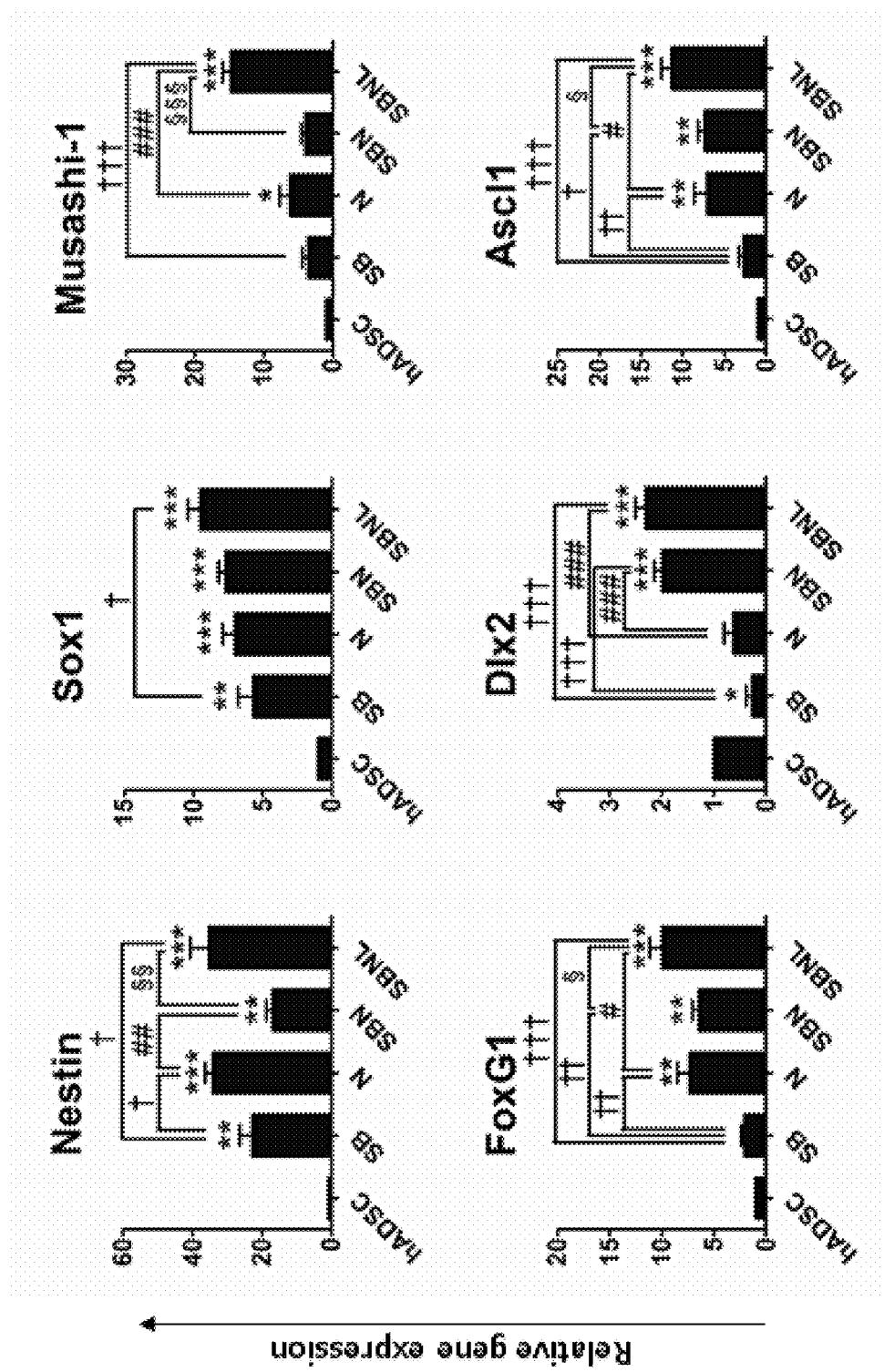

FIG. 9 is diagrams illustrating Comparative analysis of NSC induction from hADSCs using different combinations of small molecules (SMs).

*P<0.05, P<0.01, *P<0.001 compared to hADSC, †P<0.05, ††P<0.01, †††P<0.001 compared to SB, #P<0.05, ##P<0.01, ###P<0.001 compared to N, § P<0.05, §§ P<0.01, §§§ P<0.001 compared to SBN. ANOVA followed by post hoc Newman-Keuls test.

DETAILED DESCRIPTION

The present invention discloses a composition and a method for differentiation of neural stem cells, neurons and GABAergic neurons from mesenchymal stem cells, and more preferably, which includes culturing the mesenchymal stem cells in a medium containing SB431542, Noggin and LDN193189, thereby differentiating the mesenchymal stem cells into neural stem cells, neurons and GABAergic neurons at a high transformation rate without gene manipulation.

Hereinafter, the present invention will be described in detail.

The present invention provides a method for differentiation of neural stem cells from mesenchymal stem cells.

The method of the present invention includes 1) culturing the mesenchymal stem cells in a medium containing SB431542, Noggin and LDN193189.

The mesenchymal stem cell may include bone marrow-derived and/or adipose-derived mesenchymal stem cells.

SB431542 is a TGF beta signal transfer inhibitor, while Noggin and LDN193189 are BMP inhibitors.

A transforming growth factor (TGF) beta signal transfer inhibitor refers to a material preventing a signal of TGF beta family that controls a cellular process and a development process such as mitosis, cellular differentiation, embryonic pattern formation and/or organogenesis. In the present invention, the TGF beta signal inhibitor may include not only SB431542 but also any one capable of inhibiting the transfer of signals from TGF beta family such as SB202190, SB505124, NPC30345, SD093, SD908, SD208, LY2109761, LY364947, LY580276, and A-83-01, etc., without particular limitation thereof.

A small molecule BMP inhibitor ('BMP inhibitor') means a material to inhibit the binding of bone morphogenetic protein (BMP) to a BMP receptor (type I or type II). In the present invention, the BMP inhibitor may include not only Noggin and LDN 193189 but also any one capable of inhibiting the binding of BMP to BMP receptor such as chordin, follistatin and derivatives thereof, etc., without particular limitation thereof.

A medium containing SB431542, Noggin and LDN193189 may include, for example, a Dulbecco's modified eagle medium (DMEM), DMEM F-12 medium, Ham's F12 medium, glutamine, DMEM F-12:Neurobasal (1:1) or a combination thereof, and preferably, DMEM F-12 medium, but it is not limited thereto.

The medium containing SB431542, Noggin and LDN193189 preferably includes 1 to 200 μM SB431542, 0.01 to 1 μg/ml Noggin and/or 0.1 to 20 μM LDN193289, and more preferably, 5 to 20 μM SB431542, 0.05 to 0.2 μg/ml Noggin and 0.1 to 1.0 μM LDN193289 in order to increase the differentiation of neural stem cells. If departing from the above range, differentiation efficiency may be reduced.

In the medium containing SB431542, Noggin and LDN193189 as described above, 0.5 to 30% KOSR, 0.5 to 1.5% Penicillin/Streptomycin, 0.1 to 10% Glutamax, 0.1 to 10% non-essential amino acid and 1 to 500 ng/ml basic fibroblast growth factor (bFGF) may be further included.

The above medium may further include sodium pyruvate, glutamine, insulin, transferrin, sodium selenite or a combination thereof. Insulin is a peptide hormone secreted from β cell of islets of Langerhans in pancreas. Transferrin as one of β globulins is an iron-carrier protein, which is combined with three-valent iron ions in two molecules absorbed in the serum to deliver irons required for increasing cells or producing hemoglobin into the cell through a transferrin receptor as a medium. Sodium selenite is an inorganic compound represented by Formula of $Na_2SeO_3$.

Further, the medium may further include cytokine peptide factors to induce the differentiation or growth of neurons and nerve tissues such as a vascular endothelial growth factor (VEGF), a hepatocyte growth factor (HGF), a nerve growth factor (NGF), a glial cell line-derived neurotrophic factor (GDNF) and a platelet-derived growth factor (PDGF), etc.

Further, the medium may further include antibiotics, growth factors, amino acid, inhibitors or analogues thereof, as well as fetal calf serum (FCS) or fetal bovine serum (FBS), etc. Examples of these materials may include lipoic acid, albumin, hydrocortisone, insulin, etc.

The culturing may be conducted in a polypeptide-immobilized culturing dish, and the polypeptide may be a single protein or a protein composite. The single protein may include, for example, vitronectin. The protein composite may include, for example, MATRIGEL™) (BD Biosciences), but it is not limited thereto.

The culturing may be conducted for 4 to 12 days, preferably, 6 to 10 days, and more preferably, 6 to 8 days.

According to one embodiment of the present invention, the method of the present invention may include 2) culturing the cells cultured in step 1) in a medium containing B27, N2, and ascorbic acid; and 3) culturing the cells cultured in step 2) in a medium containing an epidermal growth factor (EGF) and a basic fibroblast growth factor (bFGF).

Each of the media of step 2) and step 3) may include, for example, a Dulbecco's modified eagle medium (DMEM), DMEM F-12 medium, Ham's F12 medium, glutamine, DMEM F-12:Neurobasal (1:1) or a combination thereof, and preferably, DMEM F-12:Neurobasal (1:1), but it is not limited thereto.

The medium of step 2) preferably includes 0.01 to 2 mM ascorbic acid, 0.1 to 10% B28 and 0.1 to 10% N2, but it is not limited thereto.

The medium of step 2) may further include 0.1 to 10% Glutamax, 1 to 20 mM D-glucose and/or 0.1 to 10 mM sodium pyruvate.

The culturing in step 2) may be conducted for 3 to 10 days, preferably, 3 to 7 days, and more preferably, 5 days.

The medium of step 3) preferably includes 1 to 500 ng/ml bFGF and 1 to 500 ng/ml of epidermal growth factor (EGF), but it is not limited thereto.

The medium of step 3) may further include 0.1 to 10% Glutamax, 1 to 20 mM D-glucose, 0.01 to 2 mM ascorbic acid, 0.1 to 10 mM sodium pyruvate and/or 0.1 to 10% B27, and 0.1 to 10% N2.

The culturing of step 3) may be conducted for 3 to 10 days, preferably, 5 to 9 days, and more preferably, 5 to 7 days.

Further, the present invention may provide a method for differentiation of GABAergic neurons from mesenchymal stem cells.

The method of the present invention may include 1) culturing the mesenchymal stem cells in a medium containing SB431542, Noggin and LDN193189.

According to one embodiment of the present invention, the method of the present invention may further include 2) culturing the cells cultured in step 1) in a medium containing B27, N2 and ascorbic acid; 3) culturing the cells cultured in step 2) in a medium containing purmorphamine and BDNF to differentiate the same into neurons; and 4) culturing the neurons differentiated in step 3) in a medium containing dibutyryl cyclic AMP (dbcAMP) and BDNF.

Each of the media of step 1) and step 2) may be the same medium as that of step 2) in the differentiation method of neural stem cells from mesenchymal stem cells of the present invention.

The media of step 1) and step 2) may include all of the materials included in the media of step 1) and step 2) in the differentiation method of neural stem cells from mesenchymal stem cells of the present invention, but it is not limited thereto.

The medium of step 3) may include, for example, a Dulbecco's modified eagle medium (DMEM), DMEM F-12 medium, Ham's F12 medium, glutamine, DMEM F-12:Neurobasal (1:1), or a combination thereof, and preferably, DMEM F-12:Neurobasal (1:1), but it is not limited thereto.

The medium of step 3) is preferably a medium containing 0.1 to 50 µM purmorphamine and 1 to 500 ng/ml BDNF, and more preferably, further includes 0.8 to 2.0 µM purmorphamine and 5 to 30 ng/ml BDNF in view of increasing the differentiation of neurons. If departing from the above range, differentiation efficiency may be reduced.

Further, the medium of step 3) may additionally include 0.1 to 10% Glutamax, 1 to 20 mM D-glucose, 0.01 to 2 mM ascorbic acid, 0.1 to 10 mM sodium pyruvate, 0.1 to 10% B27, and 0.1 to 10% N2, but it is not limited thereto.

The culturing of step 3) may be conducted for 7 to 16 days, preferably, 10 to 16 days, and more preferably, 12 to 14 days.

The medium of step 4) may include, for example, a Dulbecco's modified eagle medium (DMEM), DMEM F-12 medium, Ham's F12 medium, glutamine, DMEM F-12:Neurobasal (1:1) or a combination thereof, and preferably, DMEM F-12:Neurobasal (1:1), but it is not limited thereto.

The medium of step 4) preferably includes 0.01 to 1 mM dbcAMP and 1 to 500 ng/ml BDNF, and more preferably, 0.04 to 0.1 mM dbcAMP and 5 to 30 ng/ml BDNF in view of increasing the differentiation of GABAergic neurons. If departing from the above range, differentiation efficiency may be reduced.

The medium of step 4) may further include 0.1 to 10% Glutamax, 1 to 20 mM D-glucose, 0.01 to 2 mM ascorbic acid, 0.1 to 10 mM sodium pyruvate, 0.1 to 10% B27, and 0.1 to 10% N2.

The culturing of step 4) may be conducted for 10 to 40 days, preferably, 13 to 35 days, and more preferably, 18 to 30 days.

Further, the present invention may provide a composition for differentiation of neural stem cells, neurons and GABAergic neurons from mesenchymal stem cells.

The composition for cell differentiation may include SB431542, Noggin and LDN193189.

According to one embodiment of the present invention, the composition for cell differentiation preferably includes 1 to 200 µM SB431542, 0.01 to 1 µg/ml Noggin, 0.1 to 20 µM LDN193289, more preferably, 5 to 20 µM SB431542, 0.05 to 0.2 µg/ml Noggin and 0.1 to 1.0 µM LDN193289 in view of increasing the differentiation of neural stem cells, neurons and/or GABAergic neurons and, in particular, in view of increasing the differentiation of neural stem cells. If departing from the above range, differentiation efficiency may be reduced.

According to one embodiment of the present invention, the composition for cell differentiation may further include not only SB431542, Noggin and LDN193189 but also B27, N2, ascorbic acid, an epidermal growth factor (EGF) and a basic fibroblast growth factor (bFGF).

According to another embodiment of the present invention, the composition for cell differentiation may further include not only SB431542, Noggin and LDN193189 but also purmorphamine, dibutyryl cyclic AMP (dbcAMP) and BDNF.

According to one embodiment of the present invention, the composition for cell differentiation preferably includes 0.1 to 50 µM purmorphamine, 0.01 to 1 mM dbcAMP and 1 to 500 ng/ml BDNF, more preferably, 0.8 to 2.0 µM purmorphamine, 0.04 to 0.1 mM dbcAMP and 5 to 30 ng/ml BDNF in view of increasing an efficiency of the differentiation of neurons and/or GABAergic neurons and, in particular, preferably, in view of increasing the differentiation of neurons. If departing from the above range, differentiation efficiency may be reduced.

The composition for cell differentiation of the present invention may further include all types of materials able to be included in the above medium.

For instance, the composition of the present invention may include sodium pyruvate, glutamine, insulin, transferrin, sodium selenite or a combination thereof. Insulin is a peptide hormone secreted from β cell of islets of Langerhans in pancreas. Transferrin as one of β globulins is an iron-carrier protein, which is combined with three-valent iron ions in two molecules absorbed in serum to deliver irons required for increasing cells or producing hemoglobin into the cell through a transferrin receptor as a medium. Sodium selenite is an inorganic compound represented by Formula of $Na_2SeO_3$.

Further, cytokine peptide factors to induce the differentiation or growth of neurons and nerve tissues such as a vascular endothelial growth factor (VEGF), a hepatocyte growth factor (HGF), a nerve growth factor (NGF), a glial cell line-derived neurotrophic factor (GDNF) and a platelet-derived growth factor (PDGF), etc., may be further included.

In addition, antibiotics, growth factors, amino acid, inhibitors or analogues thereof, as well as fetal calf serum (FCS) or fetal bovine serum (FBS), etc. may be included. Examples of these materials may include lipoic acid, albumin, hydrocortisone, insulin, etc., but it is not limited thereto.

The composition of the present invention may be a medium.

Herein, the medium may include, for example, Dulbecco's modified eagle medium (DMEM), Ham's F12 medium, glutamine or a combination thereof, but it is not limited thereto.

Further, the present invention may provide a method for differentiation of neurons from mesenchymal stem cells.

The method of the present invention may include: 1) culturing mesenchymal stem cells in a medium containing SB431542, Noggin and LDN193189.

According to one embodiment of the present invention, the method of the present invention may further include 2) culturing the cells cultured in step 1) in a medium containing B27, N2 and ascorbic acid; 3) culturing the cells cultured in step 2) in a medium containing an epidermal growth factor (EGF) and a basic fibroblast growth factor (bFGF) to differentiate the same into neural stem cells; and 4) culturing the neural stem cells cultured in step 3) in a medium containing purmorphamine and a brain-derived neurotrophic factor (BDNF).

The media of step 1) to step 3) may be the same media as those used in step 1) to step 3) in the differentiation method of neural stem cells from mesenchymal stem cells of the present invention.

The material included in the media of step 1) to step 3) may include any material able to be included in the media of step 1) to step 3) in the differentiation method of neural stem cells from mesenchymal stem cells of the present invention, but it is not limited thereto.

The culturing of step 1) to step 3) may be conducted for the same period of time as that for step 1) to step 3) in the method for differentiation of neural stem cells from mesenchymal stem cells.

The method of step 3) may be the same medium as that used in step 4) in the differentiation method of GABAergic neurons from mesenchymal stem cells of the present invention.

The medium of step 3) may include any material able to be included in the medium of step 4) in the differentiation method of GABAergic neurons from mesenchymal stem cells of the present invention.

The culturing of step 3) may be conducted for the same period of time as that for the culturing of step 4) in the differentiation method of GABAergic neurons from mesenchymal stem cells of the present invention.

According to a particular embodiment of the present invention, adipose-derived mesenchymal stem cells were cultured in a medium for cell culture by adding SB431543, Noggin and LDN193189 as a small molecule inhibitor to the medium for 6 to 8 days (step 1: pre-treatment step), then, cultured in a medium containing B27 and N2 for 5 days (step 2: nerve induction step), and further cultured in a medium containing bFGF and EGF for 5 to 7 days (step 3: proliferation step), so as to differentiate the above stem cells into neural stem cells. As a result, it was found that an experimental group including the small molecule inhibitor showed increased expression of mRNA in neural stem cell molecular markers such as Nestin, Sox1, Pax6, Musashi-1, Vimentin, Olig2, Nkx2.1, FoxG1, Tuj1 and Ascl1, compared to a non-treatment group. Further, detection of induced neural stem cells expressing both of Nestin and Sox2 was identified through fluorescent immune cell straining (see FIGS. 1A to 1D and FIGS. 2A to 2D). Next, as a result of further differentiating the above neural stem cells in the cell culture solution of step 3) into neurons using a medium containing purmorphamine and BDNF, it was found that expression of genes associated with mature neurons was remarkably increased (see FIGS. 3A to 3C and FIG. 4A to 4C). Further, as a result of differentiating the above neurons in the cell culture solution of step 2) into GABAergic neurons using a medium containing purmorphamine, BDNF, dbcAMP and BDNF, it was found that cell molecular markers of medial ganglionic eminence (MGE) such as NKX2.1, DLX2 and LHX6 and neuron molecular markers such as TuJ1 and MAP2 were expressed. Further, it was also found in GABAergic neurons that, when a glutamic acid receptor blocking agent is present, spontaneously inhibitory post-synaptic current (IPSC) was appeared, then disappeared by treatment using a $GABA_A$ receptor blocking agent. Therefore, final differentiation of GABAergic neurons having desired functions could be identified (see FIGS. 5A to 5D and FIGS. 6A to 6D).

Accordingly, the neuron and GABAergic neuron obtained by the differentiation method of the present invention may be usefully used in developing a novel method for treatment of neurological diseases.

The mesenchymal stem cell according to the present invention may be derived from most of animals such as human, pig, monkey, horse, cattle, sheep, dog, cat, mouse or rabbit, in particular, the human, but it is not limited thereto.

The mesenchymal stem cell according to the present invention may include bone marrow-derived or adipose-derived mesenchymal stem cells, and preferably, adipose-derived mesenchymal stem cells, but it is not limited thereto.

In the present invention, "B27" and "N2" are a non-serum supplement agent, which is a component of the medium used in the method of the present invention.

According to the present invention, "bFGF" is a protein belonging to FGF family with functions of a cell proliferation, cell differentiation, as well as mitosis promoting factor, angiogenesis factor, bone morphogenic factor and nerve growth factor, is also referred to as FGF2 and known to mostly activate water-soluble proteins including FGFR 1b, FGFR 1c, FGFR 2c, FGFR 3c, and FGFR 4c, and in particular, strongly activate FGFR 1c and FGFR 3c. Not only FGF family protein activating FGFR described above but also any material capable of transferring bFGF-similar signals may be used without particular limitation thereof.

Further, the present invention may provide neural stem cells, neurons and GABAergic neurons prepared according to the above method.

In addition, the present invention may provide a composition including the neural stem cells, neurons and GABAergic neurons prepared by the above method, which may be used for: treatment of cells having nerve injury; screening of therapeutic agents for cells having nerve injury; screening of therapeutic agents for brain disease; prevention and treatment of diseases associated with optic nerve injury; and preparation of artificial retina.

The composition prepared from the mesenchymal stem cells of the present invention in each of the steps described above may be useful for preparation of neurons and GABAergic neurons having functionally and genetically similar characteristics to primary neurons and primary GABAergic neurons. Further, the finally and purely isolated neurons and GABAergic neurons may be usefully used in drug screening to develop novel therapeutic drugs for neurological diseases and analysis of drug toxicity.

Hereinafter, the present invention would be described in detail by means of the following examples and experimental examples.

The examples and experimental examples described below are only for purpose of illustrating the present invention, however, the present invention is not particularly limited to these examples and experimental examples.

Culture of Adipose-Derived Mesenchymal Stem Cells (hADSC)

In order to maintain adipose-derived mesenchymal stem cells, culturing was conducted in a medium prepared by adding 10% fatal bovine serum and 1% penicillin/streptomycin to a DMEM basic medium, and the stem cells were maintained in a 5% $CO_2$ incubator at 37° C. Next, after treating a cell-cultured dish with 0.25% trypsin-EDTA, then taking off the cells, the cells were sub-cultured with the number of $8 \times 10^4$ cells on a gelatin-coated 10 $cm^2$ tissue culture dish at an interval of 4 days. The medium was replaced with a new one every two days, and a sub-culture passage of the cells did not exceed 9.

<Experimental Example 1> Identification of Establishment of Cross-Differentiation of Pseudo-Neural Stem Cell Induced from Adipose-Derived Stem Cell <1-1> Establishment of Conditions for Three-Step Differentiation With regard to a method for cross-differentiation of neural stem cells from adipose-derived mesenchymal stem cells, initial comparison experiments were executed under a condition of using the stem cells with 3% knock out serum replacement (KOSR) without any treatment, and under another condition of using the stem cells with 3% KOSR as well as a small molecule inhibitor, thereby establishing conditions for differentiation.

The differentiation was performed generally in three steps. In a first step, the adipose-derived mesenchymal stem cells with the number of $2 \times 10^5$ cells were placed in a gelatin-coated 6 $cm^2$ dish and cultured in a 5% $CO_2$ incubator at 37° C. for 1 day. On next day, the medium was replaced with a pre-induction medium with a constitutional composition of 3% KOSR, 1% Penicillin/Streptomycin, 1% Glutamax, 1% non-essential amino acid and 4 ng/ml basic fibroblast growth factor (bFGF) in a DMEM F-12 basic medium, and the stem cells were maintained in a 5% $CO_2$ incubator at 37° C. for 8 days. In this step, the culturing condition was divided into a treatment group using 10 μM SB431542, 0.1 μg/ml Noggin and 0.5 μM LDN193289 as a small molecule inhibitor and a non-treatment group, so as to compare the differentiation of neural stem cells with each other.

Then, in a second step, the medium was replaced with a neural induction medium with a constitutional composition of 1% Glutamax, 3 mM D-glucose, 0.2 mM ascorbic acid, 1 mM sodium pyruvate, 2% B27 and 1% N2 in a DMEM F-12:Neurobasal (1:1) basic medium, and the stem cells were cultured in a 5% $CO_2$ incubator at 37° C. for 5 days.

Lastly, in a third step, the medium was replaced with a growth medium prepared by adding 20 ng/ml bFGF as a growth factor and 20 ng/ml epidermal growth factor (EGF) to a nerve induction medium, and the cells were cultured in a 5% $CO_2$ incubator at 37° C. for 7 days, in order to increase the number of pseudo-neural stem cells. Next, in order to determine whether the neural stem cells were correctly differentiated, the cells obtained after completing these three steps, were washed with PBS and 1× TryPLE select was treated in an incubator at 37° C. for to 4 minutes, followed by finely grinding the same into single cells. Then, the cells were adhered to a 6 $cm^2$ dish pre-coated with 1 μg/ml Poly-L-ornithine (PLO)/10 μg/ml Fibronectin (FN) and 4-well dish provided with 12 $mm^2$ cover glass, then, cultured in a 5% $CO_2$ incubator at 37° C. for 2 to 3 days, followed by assaying the differentiation of cells. The 6 $cm^2$ dish was subjected to real-time PCR analysis to compare the expression of target genes, while the 4-well dish having the cover glass was subjected to observation of protein expression and the form of expression through immuno-fluorescent staining.

<1-2> Identification of Gene Expression Related to Differentiation of Induced Neural Stem Cell Through Real Time PCR In order to assay a degree of gene expression in the differentiated and induced neural stem cell, sampling was executed using a cell scraper and total RNAs were isolated using a trizol reagent according to a method instructed in a manual. The isolated total RNAs were synthesized into cDNA using M-MLV reverse-transcriptase enzyme by a reaction at 42° C. for 1 hour. Using the synthesized cDNA as a template and according to SYBR Green gene expression assays, gene expressions were compared. Sequences of the target genes and primer to be compared are shown in Table 1 below. An amount of expression of target gene was standardized by endogenous GAPDH and the comparison of gene levels was executed by a Ct value comparison method of measured genes. The Ct value refers to a cycle period at which a fluorescent level reaches a critical value. ΔCt value was determined by calculating CT value, which is obtained by removing GAPDH value from [ΔCt=Ct (target)−Ct (GAPDH)] value of the target gene, while the standard expression gene was represented by a relative value to the target gene, that is, ΔCT of GAPDH=$2^{\Delta Ct}$.

TABLE 1

| Gene name | Forward(F) & reverse(R) primer sequences | Product size (bp) | Gene Bank Accession |
|---|---|---|---|
| CALB2 | F: 5'-CTCCAGGAATACACCCAAA-3' (SEQ ID NO: 1)<br>R: 5'-CAGCTCATGCTCGTCAATGT-3' (SEQ ID NO: 2) | 207 | BC015484.2 |
| Dlx2 | F: 5'-GCACATGGGTTCCTACCAGT-3' (SEQ ID NO: 3)<br>R: 5'-TCCTTCTCAGGCTCGTTGTT-3' (SEQ ID NO: 4) | 153 | BC032558.1 |
| Dlx5 | F: 5'-CCAACCAGCCAGAGAAAGAA-3' (SEQ ID NO: 5)<br>R: 5'-GCAAGGCGAGGTACTGAGTC-3' (SEQ ID NO: 6) | 150 | BC006226 |
| Emx1 | F: 5'-AAGCGCGGCTTTACCATAGAG-3' (SEQ ID NO: 7)<br>R: 5'-GCTGGGGTGAGGGTAGTTG-3' (SEQ ID NO: 8) | 150 | NM_004097.2 |
| FoxG1 | F: 5'-AGAAGAACGGCAAGTACGAGA-3' (SEQ ID NO: 9)<br>R: 5'-TGTTGAGGGACAGATTGTGGC-3' (SEQ ID NO: 10) | 189 | BC050072.1 |
| GABRA1 | F: 5'-GGATTGGGAGAGCGTGTAACC-3' (SEQ ID NO: 11)<br>R: 5'-TGAAACGGGTCCGAAACTG-3' (SEQ ID NO: 12) | 66 | BC030696 |
| GABRA2 | F: 5'-GTTCAAGCTGAATGCCCAAT-3' (SEQ ID NO: 13)<br>R: 5'-ACCTAGAGCCATCAGGAGCA-3' (SEQ ID NO: 14) | 160 | BC022488 |
| GABRA5 | F: 5'-ATCTTGGATGGGCTCTTGG-3' (SEQ ID NO: 15)<br>R: 5'-TGTACTCCATTTCCGTGTCG-3' (SEQ ID NO: 16) | 130 | BC111979 |
| GAD65 | F: 5'-GGTGGCTCCAGTGATTAAAG-3' (SEQ ID NO: 17)<br>R: 5'-TGTCCAAGGCGTTCTATTTC-3' (SEQ ID NO: 18) | 165 | M81882.1 |
| GAD67 | F: 5'-AGGCAATCCTCCAAGAACC-3' (SEQ ID NO: 19)<br>R: 5'-TGAAAGTCCAGCACCTTGG-3' (SEQ ID NO: 20) | 218 | M81883.1 |
| GFAP | F: 5'-CAACCTGCAGATTCGAGAAA-3' (SEQ ID NO: 21)<br>R: 5'-GTCCTGCCTCACATCACATC-3' (SEQ ID NO: 22) | 153 | AF419299.1 |
| Gli3 | F: 5'-TGGTTACATGGAGCCCCACTA-3' (SEQ ID NO: 23)<br>R: 5'-GAATCGGAGATGGATCGTAATGG-3' (SEQ ID NO: 24) | 116 | M57609.1 |
| LHX6 | F: 5'-GGGCGCGTCATAAAAAGCAC-3' (SEQ ID NO: 25)<br>R: 5'-TGAACGGGGTGTAGTGGATG-3' (SEQ ID NO: 26) | 108 | BC103936 |
| Map2 | F: 5'-CGCTCAGACACCCTTCAGATAAC-3' (SEQ ID NO: 27)<br>R: 5'-AAATCATCCTCGATGGTCACAAC-3' (SEQ ID NO: 28) | 122 | U01828.1 |
| Mash1 | F: 5'-TGCACTCCAATCATTCACG-3' (SEQ ID NO: 29)<br>R: 5'-GTGCGTGTTAGAGGTGATGG-3' (SEQ ID NO: 30) | 146 | NM_004316 |
| Musashi | F: 5'-TTCGGGTTTGTCACGTTTGAG-3' (SEQ ID NO: 31)<br>R: 5'-GGCCTGTATAACTCCGGCTG-3' (SEQ ID NO: 32) | 250 | AB012851.1 |
| Nestin | F: 5'-CACCTGTGCCAGCCTTTCTTA-3' (SEQ ID NO: 33)<br>R: 5'-TTTCCTCCCACCCTGTGTCT-3' (SEQ ID NO: 34) | 170 | NM_006617 |
| NKX2.1 | F: 5'-GTGAGCAAGAACATGGCCC-3' (SEQ ID NO: 35)<br>R: 5'-AACCAGATCTTGACCTGCGT-3' (SEQ ID NO: 36) | 182 | BC006221.2 |
| Olig2 | F: 5'-GCTGCGACGACTATCTTCCC-3' (SEQ ID NO: 37)<br>R: 5'-GCCTCCTAGCTTGTCCCCA-3' (SEQ ID NO: 38) | 244 | NM_005806.3 |
| Pax6 | F: 5'-AGGTATTACGAGACTGGCTCC-3' (SEQ ID NO: 39)<br>R: 5'-TCCGCTTATACTGGGCTATTT-3' (SEQ ID NO: 40) | 104 | AY047583 |
| SCN5A | F: 5'-GGATCGAGACCATGTGGGAC-3' (SEQ ID NO: 41)<br>R: 5'-GCTGTGAGGTTGTCTGCACT-3' (SEQ ID NO: 42) | 151 | BC144621 |
| Sox1 | F: 5'-AGATGCCACACTCGGAGATCA-3' (SEQ ID NO: 43) | 184 | NM_005986 |

TABLE 1-continued

| Gene name | Forward(F) & reverse(R) primer sequences | Product size (bp) | Gene Bank Accession |
|---|---|---|---|
| | R: 5'-GAGTACTTG TCCTCCTTGAGCAGC-3' (SEQ ID NO: 44) | | |
| Sox2 | F: 5'-AGTCTCCAA GCGACGAAAAA-3' (SEQ ID NO: 45) R: 5'-GCAAGAAGC CTCTCCTTGAA-3' (SEQ ID NO: 46) | 141 | NM_003106.3 |
| TuJ1 | F: 5'-GGCCTTTGG ACATCTCTTCA-3' (SEQ ID NO: 47) R: 5'-ATACTCCTC ACGCACCTTGC-3' (SEQ ID NO: 48) | 241 | BC000748.2 |
| Vimentin | F: 5'-AGAACTTTG CCGTTGAAGCTG-3' (SEQ ID NO: 49) R: 5'-CCAGAGGGAG TGAATCCAGATTA-3' (SEQ ID NO: 50) | 255 | NM_003380.3 |
| GAPDH | F: 5'-GTCAGTGGT GGACCTGACCT-3' (SEQ ID NO: 51) R: 5'-CACCACCCT GTTGCTGTAGC-3' (SEQ ID NO: 52) | 256 | BC083511.1 |

<1-3> Identification of Expression of Protein Related to Differentiation of Neural Stem Cell induced by Immuno-Fluorescent Staining The induced neural stem cells maintained on the 4-well dish was fixed using 4% formaldehyde for 15 minutes, and washed twice with phosphate buffered saline (PBS) containing calcium ions and magnesium ions. Then, the washed stem cells were treated with 0.1% diluted triton X-100 of a type of a surfactant in PBS twice at an interval of 10 minutes, in order to penetrate an antibody.

Further, in order to prevent a non-specific antibody from being adhered to the stem cells to be detected, a goat serum was diluted to 5% and added to 0.1% triton X-100/PBS and reacted with the sample for 1 hour. Types of a primary antibody adhered to the cell are different according to the cells, and target antibodies depending on proteins and dilution amounts are shown in Table 2 below.

TABLE 2

| Antibody name | Company (Cat. No.) |
|---|---|
| Anti-DLX2 | Santa Cruz (sc-81960) |
| Anti-GABA | Sigma-Aldrich (A2052) |
| Anti-GAD | Merck Millipore (AB1511) |
| Anti-GFAP | Merck Millipore (MAB3402) |
| Anti-MAP2 | Merck Millipore (MAB3418) |
| | Merck Millipore (AB5622) |
| Anti-NCAM | BD bioscience (562794) |
| Anti-Nestin | BD bioscience (611658) |
| Anti-NeuN | Merck Millipore (MAB377) |
| Anti-NFM | Merck Millipore (AB1987) |
| Anti-NKX2.1 | Merck Millipre (MAB5460) |
| Anti-Olig2 | From lab stocks (Gift of Harvard University) |
| Anti-PAX6 | Merck Millipore (MAB5554) |
| Anti-PSD96 | Merck Millipore (MABN68) |
| Anti-S100 | Dako (Z0311) |
| Aanti-SOX2 | Merck Millipore (AB5603) |

TABLE 2-continued

| Antibody name | Company (Cat. No.) |
|---|---|
| Anti-SYP | Sigma-Aldrich (SAB4502906) |
| Anti-TuJ1 | Bio Legend (PRB-435P) |

After adhering the primary antibody, the sample was reacted in a shaker at 4° C. for 16 hours. A secondary antibody was selected and used depending upon hosts and wavelengths of the primary antibody. Further, goat anti-(mouse IgG)-conjugated Alexa Fluor 555 (1:200 dilution), goat anti-(mouse IgG)-conjugated Alexa Fluor 488 (1:200 dilution), goat anti-(rabbit IgG)-conjugated Alexa Fluor 555 (1:200 dilution) and goat anti-(rabbit IgG)-conjugated Alexa Fluor 488 (1:200 dilution) were used. Further, nuclear staining was conducted using DAPI (1:1000 dilution).

The sample obtained after completion of staining was subjected to photographing and assay by means of a confocal laser-scanning microscope, that is, Carl Zeiss LSM700, the above processes are illustrated in a diagram of FIG. 1A Accordingly, as shown in FIGS. 1B to 1D, the induced neural stem cells exhibited a decreased and uniform morphology in the cross-differentiation of neural stem cells in both cases of the small molecule inhibitor treatment group and the non-treatment group (FIG. 1B). Meanwhile, as shown in FIG. 1C, mRNA expression of molecular markers of the neural stem cells such as Nestin, Sox1, Sox2, Pax6, Musashi-1, Vimentin, Olig2, Nkx2.1, FoxG1, Tuj1, and Ascl1 were all increased in both of the small molecule inhibitor treatment condition and the non-treatment condition, however, it could be seen that the small molecule inhibitor treatment group shows considerably increased expression of molecular markers of the neural stem cells, as compared to the non-treatment group (FIG. 1C). Further, neuron adhesion molecule (NCAM) was subjected to flow cytometry to conduct quantification of the induced neural stem cells by means of fluorescent assisted cell sorting (FACS) caliber (FIG. 1D).

Further, as shown in FIGS. 2A to 2D, the induced neural stem cells have neurosphere formation at DIV 4 after passage. The induced neural stem cells expressing both of Nestin and Sox2 was detected through fluorescent immune cell staining (FIG. 2B). Further, it was demonstrated that expression of molecular markers of neural stem cells and initial neurons (Sox1, Sox2, Nestin, Musashi-1, FoxG1, Nkx2.1, Pax6, Gli3, Vimentin, Tuj1 and Emx1) was varied during cross-differentiation of neural stem cells through real time PCR (FIG. 2C). The transplanted iNSCs were stained with monoclonal anti-human nuclei (hNu, red) and either polyclonal anti-SOX2 or anti-TuJ1 antibodies (green) (FIG. 2D).

<Experimental Example 2> Identification of Establishment of Differentiation of Mature Neuron from Adipose-Derived Stem Cell On the basis of the method for differentiation of neural stem cells from adipose-derived mesenchymal stem cells in <Experimental Example 1>, three-step differentiation method has been executed to obtain heterogeneous cells having characteristics similar to those of neural stem cells and, in order to differentiate these cells into mature neurons, the following experiments were executed.

More particularly, $2 \times 10^5$ cells of adipose-derived mesenchymal stem cells entered in a 6 cm² gelatin-coated dish, and cultured in a 5% $CO_2$ incubator at 37° C. overnight. On next day, the used medium was replaced with a new one prepared by adding 10 μM SB431542, 0.1 μg/ml Noggin and 0.5 μM LDN193289 as a small molecule inhibitor to a pre-induction medium containing 3% knockout serum replacement (KOSR), 1% Penicillin/Streptomycin, 1% Glutamax, 1% non-essential amino acid and 4 ng/ml bFGF in a DMEM F-12 basic medium, followed by culturing the stem cells in a 5% $CO_2$ incubator at 37° C. for 6 days. In a second step, the used medium was replaced with a new one, that is, a neural induction medium containing 2% B27 and 1% N2, followed by culturing the cells in a 5% $CO_2$ incubator at 37° C. for 5 days. Lastly, in a third step, in order to increase the number of pseudo-neural stem cells, the used medium was replaced with a growth medium prepared by adding 20 ng/ml bFGF and 20 ng/ml EGF as a growth factor to the neural induction medium, followed by culturing the cells in a 5% $CO_2$ incubator at 37° C. for 5 days. After then, in order to differentiate the cells into mature neurons, the cells obtained after completing the above three-step differentiation process were washed with PBS, and 1× TryPLE select was treated in an incubator at 37° C. for 3 to 4 minutes to finely grind the same into single cells. Then, $1×10^6$ cells were entered in a 35 $mm^2$ dish pre-coated with PLO/FN, while $1×10^5$ cells/well were entered in a 4-well dish provided with 12 $mm^2$ cover glass, then, stabilized in a 5% $CO_2$ incubator at 37° C. overnight. On next day, the used medium was replaced with a new one prepared by adding 1 μM purmorphamin and 10 ng/ml brain-derived neurotrophic factor (BDNF) to a neural induction medium, followed by culturing the same in a 5% $CO_2$ incubator at 37° C. for 12 to 14 days while replacing the medium with new ones every third day.

Accordingly, as shown in FIGS. 3A to 3C, the induced neurons had a morphology of mature neurons, which is different from bipolar or multipolar neuritis from the cell body (FIG. 3B).

Further, as a result of identifying changes in expressions of molecular markers of neurons such as Tuj1 and MAP2, transcription factors (FoxG1, Nkx2.1, Pax6, Dlx2, Dlx5 and Lhx6) relevant to medial ganglionic eminence (MGE), which are expressed at the initial and late stages of the development process, an initial GABA molecular marker (GAD67) and a sodium ion channel gene (SCN5A) according to quantification through real time PCR, it was demonstrated that the expression of genes relevant to mature neurons in the induced neurons was noticeably increased (FIG. 3C).

Further, as shown in FIGS. 4A to 4C, it could be seen that neuron molecular markers relevant to brain development, for example, neuron precursor molecular markers (TuJ1/Pax6), mature neuron molecular markers (NeuN/MAP2), astrocyte molecular markers (GFAP/S100), early oligodendrocyte molecular marker (Olig2) have been expressed in the induced neurons (FIG. 4A), and a rate of the number of the induced neurons expressing the above molecular markers alone or in a combination thereof was quantitatively identified (FIG. 4B). Further, FIG. 4C illustrates an electrical and physiological record sample measured from the induced neurons having a typical form of neurons, and the induction of action potential by current input. A current input protocol is indicated below the action potential record, while the record at the bottom end indicates a representative spontaneous synapse action obtained from the induced neurons in a fixed voltage clamp mode (−60 mV fixed). Further, the enlarged single current is represented below the continuously indicated record (FIG. 4C).

<Experimental Example 3> Identification of Establishment of Differentiation of GABAergic Neuron from Adipose-Derived Stem Cell Similarly, on the basis of the three-step differentiation method executed in <Experimental Example 1>, the method for differentiation of GABAergic neurons from adipose-derived mesenchymal stem cells has been established. In order to increase the number of days culturing in the neuron maturation medium, the number of days of cross-differentiation of neural stem cells from adipose-derived mesenchymal stem cells was shortened. Next the neuron induction medium comprising purmorphamine and BDNF and the neuron maturation medium comprising dbcAMP and BDNF were used.

More particularly, $2×10^5$ cells of adipose-derived mesenchymal stem cells entered in a 6 $cm^2$ gelatin-coated dish, and were cultured in a 5% $CO_2$ incubator at 37° C. overnight. On next day, the used medium was replaced with a new one prepared by adding 10 μM SB431542, 0.1 μg/ml Noggin and 0.5 μM LDN193289 as a small molecule inhibitor to a pre-induction medium containing 3% KOSR, 1% Penicillin/Streptomycin, 1% Glutamax, 1% non-essential amino acid and 4 ng/ml bFGF in a DMEM F-12 basic medium, followed by culturing the stem cells in a 5% $CO_2$ incubator at 37° C. for 6 days. After finishing the culturing of step 1), the cells were washed with PBS and 1× TryPLE select was treated in an incubator at 37° C. for 3 to 4 minutes to finely grind the same into single cells. Then, $1×10^6$ cells were entered in a 35 $mm^2$ dish pre-coated with PLO/FN, while $1×10^5$ cells per well were entered in a 4-well dish provided with 12 $mm^2$ cover glass, then, stabilized in a 5% $CO_2$ incubator at 37° C. overnight. In a second step, the used medium was replaced with a new one, that is, a neural induction medium containing 2% B27 and 1% N2, followed by culturing the cells in a 5% $CO_2$ incubator at 37° C. for 5 days. After then, in order to differentiate the cells into GABAergic neurons, the used medium was replaced with a new medium containing 1 μM purmorphamine and 10 ng/ml BDNF, followed by culturing the cells in a 5% $CO_2$ incubator at 37° C. for 10 to 14 days while replacing the used medium into new ones every third day. After differentiating the cells into neurons for 10 to 14 days, in order to induce the differentiation of GABAergic neurons, 50 μM dbcAMP and 20 ng/ml BDNF were added to the neural induction medium, followed by culturing the cells for 13 to 20 days.

As a result, as shown in FIGS. 5A to 5D, the induced GABAergic neurons exhibited a number of radial neuritis extending from a neurosphere-like cell group, and it was identified that a large number of the induced GABAergic neurons have expressed cell molecular markers of medial ganglionic eminence (MGE) such as NKX2.1, DLX2 and LHX6, etc. and neuron molecular markers such as TuJ1 and MAP2, etc. (FIG. 5B). Further, a rate of the number of the induced neurons expressing the above molecular markers alone or in a combination thereof was quantitatively identified (FIG. 5C). Further, it can be seen that the induced GABAergic neurons exhibited neuritis radiating from the neurosphere-like cell cluster while expressing neuro-filament molecular marker, that is, neuro-filament M (NF-M) (FIG. 5D).

Further, as shown in FIGS. 6A to 6D, as a result of the real time PCR assay, changes in gene expression of neuron (MAP2), medial ganglionic eminence (MGE) transcription factors (Dlx2 and Dlx5), astrocyte molecular marker (GFAP), calcium-conjugated protein (CALB2), GABAergic receptors (GABRA1, GABRA2 and GABRA5) and GABA (GAD65 and GAD67) were identified. Most of the induced GABAergic neurons with a longer period of differentiation days on day 32 of tube culture showed drastically increased gene expression of mature GABAergic neuron, compared to the induced GABAergic neurons on day 25 of tube culture. On the other hand, relatively reduced gene expression of initial GABAergic neurons was exhibited (see FIG. 6A). Further, the fluorescent immune cell staining assay demonstrated that the induced GABAergic neurons had expression of both of GABAergic neurons molecular markers and mature neurons thereof (GABA/MAP2, GAD/MAP2, PSD95/MAP2 and PSD95/SYP) (FIG. 6B), and these results were quantitatively identified (FIG. 6C). Further, as shown in the bottom right side of FIG. 6D, it was found that, when a glutamic acid receptor blocking agent (50M APV and 20M CNQX) is present, spontaneously inhibitory post-synaptic current (IPSC) was appeared, and then, disappeared by treatment using 10M bicuculline as a $GABA_A$ receptor blocking agent (FIG. 6D).

<Experimental Example 4> Microarray Analysis of iNSCs and iGNs Induced from hADSCs For further insight into the induction route, gene expression profiles over neural induction process was investigated by microarray analysis (FIG. 7A). To confirm whether iNSCs induced from hADSCs can maintain their gene expression signatures during serially passaged culture, iNSCs at different passage numbers were included in microarray analysis. We also used the neuronally differentiated ReN VM and CX cells as positive controls of human neurons.

The Gene Ontology (GO) analysis revealed that genes involved in biological processes of nervous system development, generation of neurons and neuron differentiation were highly expressed in both iGNs and differentiated ReNcells, indicating that iGNs acquired genetic characteristics of mature neurons (FIG. 7B).

During induction of hADSCs into iNSCs and iGNs, genes associated with regulation of cell differentiation/development were upregulated, whereas genes involved in hADSC functions, such as cell adhesion and extracellular matrix organization, were downregulated (FIG. 7B). Principle component analysis showed that iGNs/differentiated ReNcells, iNSCs P0/P1/P2, and hADSCs were clustered and well-distinct (FIG. 7C). In addition, the heatmap analysis of 8 neural cell- and 4 hADSC-enriched gene expressions demonstrated that neural genes were upregulated, but hADSC genes were significantly downregulated in iNSCs, iGNs and ReNcells (FIG. 7D). Furthermore, we performed REACTOME pathway-enrichment analysis and identified REACT_13685:Synaptic Transmission as statistically significant pathway related to the differentially expressed genes in iGNs. Taken together, these results indicate the efficient induction of hADSCs into neural cells.

TABLE 3

|  |  | hADSC1 | hADSC2 | hADSC3 |
|---|---|---|---|---|
| Positive markers | CD73 | 98.83% | 99.74% | 99.21% |
|  | CD90 | 99.98% | 100% | 99.92% |
|  | CD105 | 99.63% | 99.79% | 98.89% |
|  | HLA-ABC | 97.03% | 99.11% | 94.06% |
| Negative markers | CD34 | 0.47% | 1.06% | 0.35% |
|  | CD45 | 0.03% | 0.14% | 0.39% |
|  | HLR-DR | 0.03% | 0.10% | 0.44% |

<Experimental Example 5> Comparative Analysis of NSC Induction from hADSCs Using Different Concentrations of Knock-Out Serum (KOSR)

As shown in FIG. 8, the efficiency of NSC induction protocols using different concentrations of KOSR (5% and 3%) was investigated by detecting the proportion of neural cell adhesion molecule (NCAM)-positive cells by flow cytometry. We found out that both 5% and 3% of KOSR concentrations produced similar NSC induction efficiency, approximately 60%, after measuring NCAM-positive cells using flow cytometry analysis (FIG. 8). Thus, we have decided to use 3% of KOSR for NSC induction of hADSCs.

<Experimental Example 6> Comparative Analysis of NSC Induction from hADSCs Using Different Concentrations of Small Molecules (SMs)

As shown in FIG. 9, The NSC marker expressions of cells induced from hADSCs using different combinations of SMs, SB (SB431543), N (noggin), SBN, and SBNL (LDN193189), were investigated by real-time PCR analysis. Nestin, Sox1, Musashi-1, FoxG1, and Ascl1 were significantly increased in SBNL conditions. The quantitative analysis of NSC marker expression revealed the most efficient SM treating condition for NSC induction; combination of all three compounds (FIG. 9).

What is claimed is:

1. A method for differentiation of neural stem cells from adipose-derived mesenchymal stem cells, the method comprising:
    first-culturing the adipose-derived mesenchymal stem cells in a medium containing SB431542, Noggin and LDN193189;
    second-culturing the first-cultured cells in a medium containing B27, N2 and ascorbic acid; and
    third-culturing the second-cultured cells in a medium containing epidermal growth factor (EGF) and basic fibroblast growth factor (bFGF).

2. The method according to claim 1, wherein the SB431542 is included in an amount of 1 to 200 µM, the Noggin is included in an amount of 0.01 to 1 µg/ml, and the LDN193189 is included in an amount of 0.1 to 20 µM.

3. The method according to claim 1, wherein the SB431542 is included in an amount of 5 to 20 µM, the Noggin is included in an amount of 0.05 to 0.2 µg/ml, and the LDN193189 is included in an amount of 0.1 to 1.0 µM.

4. The method according to claim 1, wherein the first-culturing is conducted for 4 to 12 days.

5. The method according to claim 1, wherein the second-culturing is conducted for 3 to 10 days; and
    the third-culturing is conducted for 3 to 10 days.

6. A method for differentiation of GABAergic neurons from adipose-derived mesenchymal stem cells, the method comprising:
    first-culturing the adipose-derived mesenchymal stem cells in a medium containing SB431542, Noggin and LDN193189;
    second-culturing the first-cultured cells in a medium containing B27, N2 and ascorbic acid;
    third-culturing the second-cultured cells in a medium containing purmorphamine and BDNF to differentiate the cells into neurons; and
    fourth-culturing the differentiated neurons in a medium containing dbcAMP and BDNF.

7. The method according to claim 6, wherein the SB431542 is included in an amount of 1 to 200 µM, the Noggin is included in an amount of 0.01 to 1 μg/ml, and the LDN193189 is included in an amount of 0.1 to 20 μM, in the first-culturing.

8. The method according to claim 6, wherein the purmorphamine is included in an amount of 1 to 50 μM, and the BDNF is included in an amount of 1 to 500 ng/ml, in the third-culturing.

9. The method according to claim 6, wherein the dbcAMP is included in an amount of 0.01 to 1 mM, and the BDNF is included in an amount of 1 to 500 ng/ml, in the fourth-culturing.

10. The method according to claim 6, wherein the first-culturing is conducted for 4 to 12 days.

11. The method according to claim 6, wherein the second-culturing is conducted for 3 to 10 days;
the third-culturing is conducted for 7 to 16 days; and
the fourth-culturing is conducted for 10 to 40 days.

* * * * *